United States Patent
Xu

(10) Patent No.: US 9,427,491 B2
(45) Date of Patent: Aug. 30, 2016

(54) BONE PASTES COMPRISING BIOFUNCTIONALIZED CALCIUM PHOSPHATE CEMENTS WITH ENHANCED CELL FUNCTIONS FOR BONE REPAIR

(71) Applicant: UNIVERSITY OF MARYLAND, BALTIMORE, Baltimore, MD (US)

(72) Inventor: Huakun Xu, Frederick, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/352,203

(22) PCT Filed: Oct. 12, 2012

(86) PCT No.: PCT/US2012/059985
§ 371 (c)(1),
(2) Date: Apr. 16, 2014

(87) PCT Pub. No.: WO2013/059089
PCT Pub. Date: Apr. 25, 2013

(65) Prior Publication Data
US 2014/0294985 A1      Oct. 2, 2014

Related U.S. Application Data

(60) Provisional application No. 61/550,083, filed on Oct. 21, 2011.

(51) Int. Cl.
| | |
|---|---|
| *A61L 24/02* | (2006.01) |
| *A61L 24/04* | (2006.01) |
| *A61L 24/08* | (2006.01) |
| *A61L 24/00* | (2006.01) |
| *A61L 24/10* | (2006.01) |
| *A61L 27/12* | (2006.01) |
| *A61L 27/20* | (2006.01) |
| *A61L 27/22* | (2006.01) |
| *A61L 27/36* | (2006.01) |
| *A61L 27/38* | (2006.01) |
| *A61L 27/54* | (2006.01) |
| *A61L 27/56* | (2006.01) |

(52) U.S. Cl.
CPC ........ *A61L 24/0042* (2013.01); *A61L 24/0005* (2013.01); *A61L 24/0015* (2013.01); *A61L 24/0036* (2013.01); *A61L 24/02* (2013.01); *A61L 24/043* (2013.01); *A61L 24/08* (2013.01); *A61L 24/106* (2013.01); *A61L 24/108* (2013.01); *A61L 27/12* (2013.01); *A61L 27/20* (2013.01); *A61L 27/227* (2013.01); *A61L 27/365* (2013.01); *A61L 27/3616* (2013.01); *A61L 27/3633* (2013.01); *A61L 27/3834* (2013.01); *A61L 27/54* (2013.01); *A61L 27/56* (2013.01); *A61L 2430/02* (2013.01)

(58) Field of Classification Search
None
See application file for complete search history.

(56) References Cited

U.S. PATENT DOCUMENTS

| | | |
|---|---|---|
| 5,294,446 A | 3/1994 | Schlameus et al. |
| 2002/0055143 A1 | 5/2002 | Bell et al. |
| 2002/0197261 A1 | 12/2002 | Li et al. |
| 2006/0067973 A1 | 3/2006 | Schachter |
| 2006/0159717 A1 | 7/2006 | Xu et al. |
| 2007/0160681 A1 | 7/2007 | Park et al. |
| 2008/0138416 A1 | 6/2008 | Rauh et al. |
| 2010/0125240 A1* | 5/2010 | Spedden et al. ............... 604/37 |
| 2011/0223142 A1 | 9/2011 | Sanford et al. |

OTHER PUBLICATIONS

Montufar et al. J Mater Sci: Mater Med. 21:863-869; Oct. 30, 2009.*
Bi et al. Biomaterials. 31:3201-3211; Feb. 8, 2010.*
Ginebra et al. Acta Biomaterialia. 6:2863-2873; Feb. 1, 2010.*
Zhou et al. Biomaterials 32(30):7503-7513; Jul. 14, 2011.*
Ho et al. Biomaterials 26;3197-3206; 2005.*
International Search Report for PCT/US2012/059985, dated Mar. 29, 2013.
Hesaraki, S. et al., Formation of interconnected macropores in apatitic calcium phosphate bone cement with the use of an effervescent additive, Journal of Biomedical Materials Research Part A, 2007, vol. 83A, No. 1, pp. 80-87.
Extended European Search Report, dated Jul. 2, 2015, in corresponding European Patent Application 12841976.9.

* cited by examiner

*Primary Examiner* — Amber D Steele
*Assistant Examiner* — Schuyler Milton
(74) *Attorney, Agent, or Firm* — Wenderoth, Lind & Ponack, L.L.P.

(57) ABSTRACT

The invention provides injectable, biofunctional agent-containing calcium phosphate cement bone pastes for bone tissue engineering, and methods of making and using the same.

23 Claims, 13 Drawing Sheets

Figure 5 con.'t
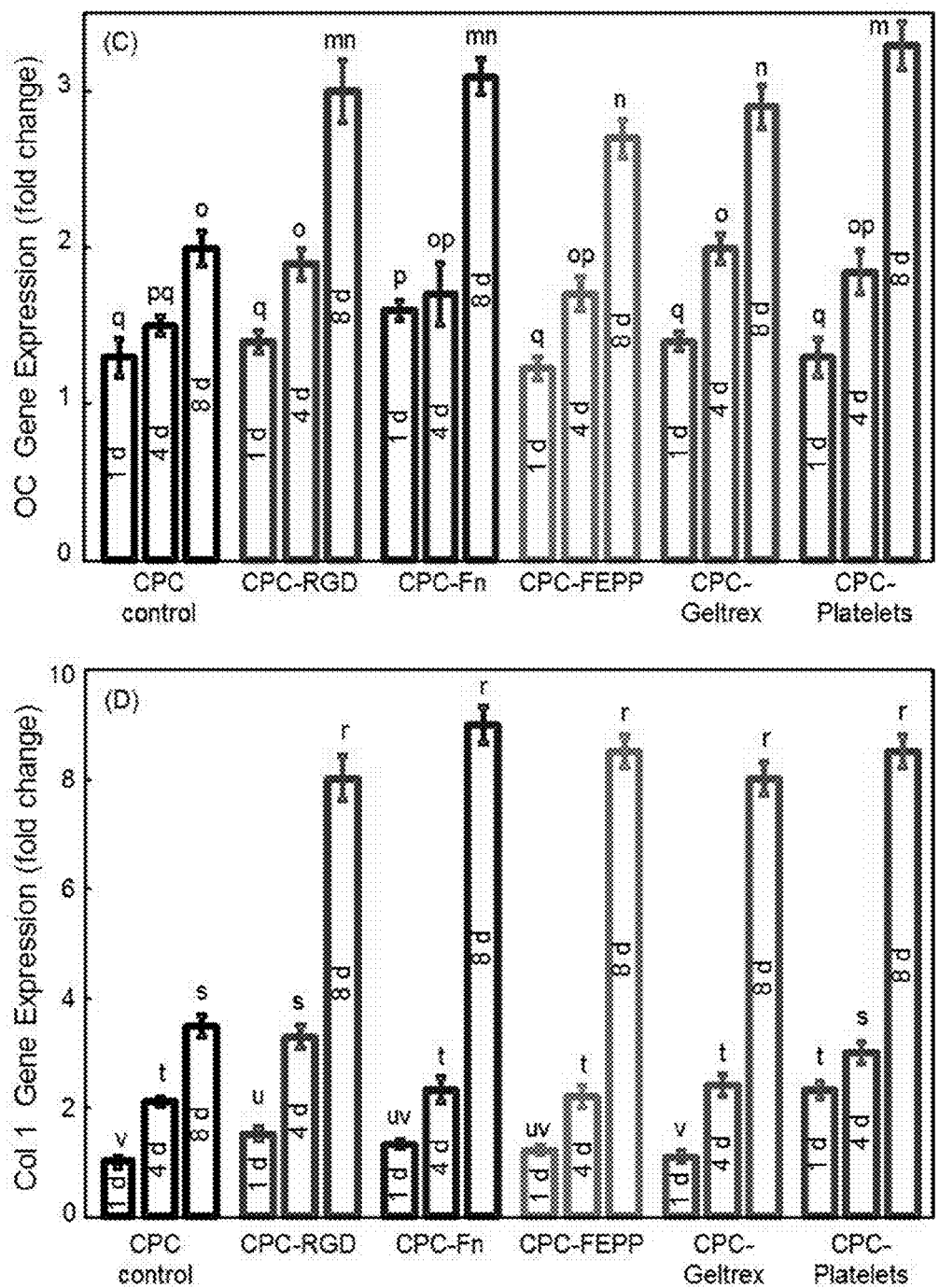

BONE PASTES COMPRISING BIOFUNCTIONALIZED CALCIUM PHOSPHATE CEMENTS WITH ENHANCED CELL FUNCTIONS FOR BONE REPAIR

STATEMENT OF GOVERNMENT SUPPORT

This invention was made with government support under Grant No. DE014190 awarded by the National Institutes of Health. The government has certain rights in the invention.

FIELD

The invention provides injectable, biofunctional agent-containing calcium phosphate cement bone pastes for bone tissue engineering, and methods of making and using the same.

BACKGROUND

Bone transplantation is used to treat bone defects arising from trauma, disease, congenital deformity, or tumor resection. Bone is the second most transplanted tissue after blood; however, current bone transplantation methods involve certain disadvantages. For example, bone autografts (i.e., bone harvested from a patient to be treated) are of limited availability and incur donor site morbidity. Bone allografts (i.e., bone harvested from a person who is not the patient to be treated) carry a risk of disease transmission. With seven million bone fractures per year in the U.S., and musculo-skeletal conditions costing $215 billion [1,2], new biomaterial treatments are needed.

Calcium phosphate cements (CPCs) can be molded and set in situ to form hydroxyapatite, they are highly osteoconductive, and they can be resorbed and replaced by new bone. Recent studies have developed CPC into a carrier for stem cell delivery to enhance bone regeneration. Stem cell-based tissue engineering has immense potential to regenerate damaged and diseased tissues [3-7].

Human bone marrow mesenchymal stem cells (hBMSCs) can differentiate into osteoblasts, adipocytes, chondrocytes, myoblasts, neurons, and fibroblasts [8-10]. hBMSCs can be harvested from a patient, expanded in culture, induced to differentiate, and combined with a scaffold to repair bone defects. However, harvesting of autogenous hBMSCs requires an invasive procedure. Moreover, autogenous hBMSCs display lower self-renewal potential with aging of the individual from whom the cells are obtained.

Human umbilical cord mesenchymal stem cells (hUCMSCs) have been used in tissue engineering [11-16]. Umbilical cords can provide an inexpensive and inexhaustible stem cell source, without the invasive procedure of hBMSCs, and without the controversies of embryonic stem cells (hESCs). hUCMSCs are primitive MSCs that exhibit a high plasticity and developmental flexibility and appear to cause no immunorejection in vivo [12]. hUCMSCs have been cultured on tissue culture plastic [13], polymer scaffolds [16], and calcium phosphate scaffolds for tissue engineering [17-19].

Calcium phosphate (CaP) scaffolds are important for bone repair because they are bioactive, mimic the bone minerals, and can bond to neighboring bone, in contrast to bioinert implants that can form undesirable fibrous capsules [20-22]. The CaP minerals provide a preferred substrate for cell attachment and expression of the osteoblast phenotype [23, 24]. However, for pre-formed bioceramic scaffolds to fit into a bone cavity, a surgeon must machine the graft or carve the surgical site, leading to increases in bone loss, trauma, and surgical time [2]. Pre-formed scaffolds have other drawbacks, including the difficulty in seeding cells deeply into the scaffold and the inability to inject such scaffolds in minimally-invasive surgeries [2,10].

Injectable scaffolds for cell delivery are advantageous because they can: (i) shorten the surgical operation time; (ii) minimize the damaging effects of large muscle retraction; (iii) reduce postoperative pain and scar size; (iv) achieve rapid recovery; and (v) reduce cost. Various injectable hydrogel and polymer carriers can be used for stem cell delivery [10,25]. However, current injectable carriers cannot be used in load-bearing repairs [10,25], such as those required in bone. For example, hydrogel scaffolds do not possess the mechanical strength to be used in load bearing applications [25].

Mechanical properties of scaffolding materials are of crucial importance in regeneration of load-bearing tissues such as bone. Specifically, scaffolding materials must be able to withstand stresses to avoid scaffold fracture and to maintain scaffold structure to define the shape of the regenerated tissue. However, to date, an injectable, bioactive, and strong scaffold for stem cell encapsulation and bone engineering has not yet been developed.

Hydroxyapatite (HA) and other calcium phosphate (CaP) bioceramics are useful in hard tissue repair because of their excellent biocompatibility [5,8,10,20-24]. When implanted into an osseous site, bone bioactive materials such as HA and other CaP implants and coatings provide an ideal environment for cellular reaction and colonization by osteoblasts. This leads to a tissue response termed osteoconduction in which bone grows on and bonds to the implant, promoting a functional interface. These bioceramics are highly useful for bone repair. However, one drawback is that sintered HA implants are generally not resorbable. Another limitation is that these bioceramics are pre-forms that require machining and may leave gaps when fitted into a bone cavity.

In contrast to CaP bioceramics, calcium phosphate cements (CPCs) can self-set in the bone site with intimate adaptation to complex shapes, they can be easily contoured for esthetics in craniofacial repairs, and they are highly osteoconductive and bioresorbable [26-32]. CPCs can be injected or molded, and set in situ to form a bioactive scaffold that bonds to bone [26-29]. The first CPC was approved by the Food and Drug Administration (FDA) in 1996 for craniofacial repairs [26,30-32]. CPC has excellent osteoconductivity and can be replaced by new bone [30-32]. However, several previous studies showed that human stem cell attachment on CPC is relatively poor. Therefore, there is a need to improve the cell attachment to CPC to enhance bone repair efficacy.

SUMMARY

Provided herein are injectable, self-setting, biofunctional agent-containing, and mechanically-strong bone pastes for bone tissue engineering. The bone pastes employ a calcium phosphate cement and one or more biofunctional agents, and optionally, additional components, such as chitosan and/or fibers for reinforcement, and a porogen to increase porosity of the pastes. In a further optional aspect, the bone pastes include cells or cell-encapsulating microbeads. In particular further aspects, the cells are stem cells.

In particular, and in a first aspect, described herein are bone pastes comprising a calcium phosphate cement and one or more biofunctional agents. The biofunctional agents include RGD-containing peptides, fibronectin, fibronectin-like engineered polymer protein (FEPP), extracellular matrix (ECM), and platelet concentrate. Thus, in a first embodiment, the bone paste comprises calcium phosphate cement and a RGD-containing peptide. The RGD-containing peptide is present within a range of about 0.0005% to about 5% by mass. The RGD-containing peptide can be, e.g., RGD, G4RGDSP, RGDS, GRGD, GRGDGY, RGDSGGC, GRGDS, or another RGD-containing polypeptide. In a second embodiment, the bone paste comprises calcium phosphate cement and fibronectin. The fibronectin is present within a range of about 0.0005% to about 5% by mass. In a third embodiment, the bone paste comprises calcium phosphate cement and FEPP. The FEPP is present within a range of about 0.0005% to about 5% by mass. In a fourth embodiment, the bone paste comprises calcium phosphate cement and ECM. The ECM is present within a range of about 0.001% to about 10% by mass. The ECM may be derived ECM (dECM). In a fifth embodiment, the bone paste comprises calcium phosphate cement and platelet concentrate. The platelet concentrate is present within a range of about 0.001% to about 10% by mass. In further embodiments, the bone paste comprises calcium phosphate cement and any two of the biofunctional agents, or any three of the biofunctional agents, or any four of the biofunctional agents, or each of the five biofunctional agents.

The calcium phosphate cement of the bone paste may comprise, for example, but not be limited to, one or more ingredients selected from the group consisting of tetracalcium phosphate (TTCP) ($Ca_4(PO_4)_2O$), dicalcium phosphate anhydrous (DCPA) ($CaHPO_4$), dicalcium phosphate dihydrate ($CaHPO_4.2H_2O$), tricalcium phosphate ($Ca_3[PO_4]_2$), α-tricalcium phosphate (α-$Ca_3(PO_4)_2$), β-tricalcium phosphate (β-$Ca_3(PO_4)_2$), octacalcium phosphate ($Ca_8H_2(PO_4)_6.5H_2O$), amorphous calcium phosphate ($Ca_3(PO_4)_2$), calcium carbonate ($CaCO_3$), calcium hydroxide ($Ca[OH]_2$), and hydroxyapatite ($Ca_{10}(PO_4)_6(OH)_2$), and mixtures thereof.

In one embodiment, the calcium phosphate cement comprises tetracalcium phosphate and dicalcium phosphate anhydrous. In this embodiment, the calcium phosphate cement may comprise, for example, but not be limited to, a molar ratio of tetracalcium phosphate to dicalcium phosphate anhydrous of about 1:5 to about 5:1, a molar ratio of tetracalcium phosphate to dicalcium phosphate anhydrous of about 1:3 to about 1:1, or the calcium phosphate cement comprises an approximately 1:1 molar ratio of tetracalcium phosphate to dicalcium phosphate anhydrous.

The calcium phosphate cement of the bone paste may further comprise chitosan. When chitosan is present, the RGD-containing peptide may be covalently linked to the chitosan.

The calcium phosphate cement of the bone paste may further comprise fibers. The fibers may be, but are not limited to, degradable fibers.

The calcium phosphate cement of the bone paste may further comprise chitosan and fibers, including, but not limited to, degradable fibers.

The calcium phosphate cement of the bone paste may further comprise a porogen. As an example, but not a limitation, the porogen may be $NaHCO_3$ and citric acid. When the porogen is $NaHCO_3$ and citric acid, the mass fraction of $NaHCO_3$ may be from about 5% to about 30%, and the mass fraction of citric acid may be from about 50% to about 60%.

The bone paste may further comprise a bioactive agent. The bone paste may also be injectable.

The bone paste may further comprise cells. When present, the cells include, but are not limited to, human umbilical cord mesenchymal stem cells, bone marrow stem cells, embryonic stem cells, pluripotent stem cells, induced pluripotent stem cells, multipotent stem cells, progenitor cells, and osteoblasts. The cells may be attached to a surface of the bone paste, or the cells may be interspersed throughout the bone paste, or both.

In a second aspect, described herein are bone pastes comprising a calcium phosphate cement, one or more biofunctional agents, and cell-encapsulating microbeads. The biofunctional agents include RGD-containing peptides, fibronectin, fibronectin-like engineered polymer protein (FEPP), extracellular matrix (dECM), and platelet concentrate. Thus, in a first embodiment, the bone paste comprises calcium phosphate cement, a RGD-containing peptide, and cell-encapsulating microbeads. The RGD-containing peptide is present within a range of about 0.0005% to about 5% by mass. The RGD-containing peptide can be, e.g., RGD, G4RGDSP, RGDS, GRGD, GRGDGY, RGDSGGC, GRGDS, or another RGD-containing peptide. In a second embodiment, the bone paste comprises calcium phosphate cement, fibronectin, and cell-encapsulating microbeads. The fibronectin is present within a range of about 0.0005% to about 5% by mass. In a third embodiment, the bone paste comprises calcium phosphate cement, FEPP, and cell-encapsulating microbeads. The FEPP is present within a range of about 0.0005% to about 5% by mass. In a fourth embodiment, the bone paste comprises calcium phosphate cement, ECM, and cell-encapsulating microbeads. The ECM is present within a range of about 0.001% to about 10% by mass. The ECM may be derived ECM (dECM). In a fifth embodiment, the bone paste comprises calcium phosphate cement, platelet concentrate, and cell-encapsulating microbeads. The platelet concentrate is present within a range of about 0.001% to about 10% by mass. In further embodiments, the bone paste comprises calcium phosphate cement, cell-encapsulating microbeads, and any two of the biofunctional agents, or any three of the biofunctional agents, or any four of the biofunctional agents, or each of the five biofunctional agents.

The calcium phosphate cement of the bone paste may comprise, for example, but not be limited to, one or more ingredients selected from the group consisting of tetracalcium phosphate (TTCP) ($Ca_4(PO_4)_2O$), dicalcium phosphate anhydrous (DCPA) ($CaHPO_4$), dicalcium phosphate dihydrate ($CaHPO_4.2H_2O$), tricalcium phosphate ($Ca_3[PO_4]_2$), α-tricalcium phosphate (α-$Ca_3(PO_4)_2$), β-tricalcium phosphate (β-$Ca_3(PO_4)_2$), octacalcium phosphate ($Ca_8H_2(PO_4)_6.5H_2O$), amorphous calcium phosphate ($Ca_3(PO_4)_2$), calcium carbonate ($CaCO_3$), calcium hydroxide ($Ca[OH]_2$), and hydroxyapatite ($Ca_{10}(PO_4)_6(OH)_2$), and mixtures thereof.

In one embodiment, the calcium phosphate cement comprises tetracalcium phosphate and dicalcium phosphate anhydrous. In this embodiment, the calcium phosphate cement may comprise, for example, but not be limited to, a molar ratio of tetracalcium phosphate to dicalcium phosphate anhydrous of about 1:5 to about 5:1, a molar ratio of tetracalcium phosphate to dicalcium phosphate anhydrous of about 1:3 to about 1:1, or the calcium phosphate cement comprises an approximately 1:1 molar ratio of tetracalcium phosphate to dicalcium phosphate anhydrous.

The calcium phosphate cement of the bone paste may further comprise chitosan. When chitosan is present, the RGD-containing peptide may be covalently linked to the chitosan.

The calcium phosphate cement of the bone paste may further comprise fibers. The fibers may be, but are not limited to, degradable fibers.

The calcium phosphate cement of the bone paste may further comprise chitosan and fibers, including, but not limited to, degradable fibers.

The calcium phosphate cement of the bone paste may further comprise a porogen. As an example, but not a limitation, the porogen may be $NaHCO_3$ and citric acid. When the porogen is $NaHCO_3$ and citric acid, the mass fraction of $NaHCO_3$ may be from about 5% to about 30%, and the mass fraction of citric acid may be from about 50% to about 60%.

The bone paste may further comprise a bioactive agent. The bone paste may also be injectable.

The microbeads of the bone paste can include hydrogel microbeads, for example, but not limited to, microbeads comprising alginate, partially oxidized alginate, oxidized alginate, alginate-fibrin, partially oxidized alginate-fibrin, oxidized alginate-fibrin, poly(ethylene glycol) diacrylate), poly(ethylene glycol)-anhydride dimethacrylate, gelatin, chemically cross-linked polymers, ionically cross-linked polymers, heat-polymerized polymers, or photopolymerized polymers. In one embodiment, the microbeads are alginate-fibrin microbeads. When the microbeads are alginate-fibrin microbeads they may comprise a fibrinogen mass fraction of from about 0.05% to about 1%, such as, but not limited to, a fibrinogen mass fraction of about 0.1%. The alginate may be at about 7.5% oxidation.

The microbeads of the bone paste may be present in a volume of about 40 to 60%, and they may have an average diameter of less than about 2 millimeters.

The cells of the bone paste may be stem cells, for example, but not limited to, one or more of human umbilical cord mesenchymal stem cells, bone marrow stem cells, stem cells from breast milk or other body fluids, embryonic stem cells, pluripotent stem cells, induced pluripotent stem cells, multipotent stem cells, progenitor cells, and osteoblasts.

The bone paste may further comprise a bioactive agent. The bone paste may also be injectable.

In a third aspect, described herein is a method for preparing a bone paste, comprising covalently linking an RGD-containing peptide to chitosan to form RGD-grafted chitosan, dissolving the RGD-grafted chitosan in water to form a chitosan liquid, and mixing calcium phosphate cement into the chitosan liquid, thereby preparing a bone paste. The RGD-containing peptide can be, e.g., RGD, G4RGDSP, RGDS, GRGD, GRGDGY, RGDSGGC, GRGDS, or another RGD-containing peptide. The RGD-containing peptide is present within a range of about 0.0005% to about 5% by mass. The chitosan may be chitosan lactate. A degradable fiber may be added to the chitosan liquid prior to mixing calcium phosphate cement into the chitosan liquid. The calcium phosphate cement may comprise an approximately 1:1 molar ratio of tetracalcium phosphate to dicalcium phosphate anhydrous.

In a fourth aspect, described herein is a method of repairing or remodeling a bone, comprising administering to a bone an effective amount of any of the bone pastes described herein and allowing the bone paste to harden, thereby repairing or remodeling the bone.

Percentage of live cells, and (B) live cell density. CPC-grafted-RGD had the highest percentages of live cells. CPC-grafted-RGD had the most live cell density per mm2. Each value is the mean of five measurements, with the error bar showing one standard deviation (mean±sd; n=5).

Figure 10:
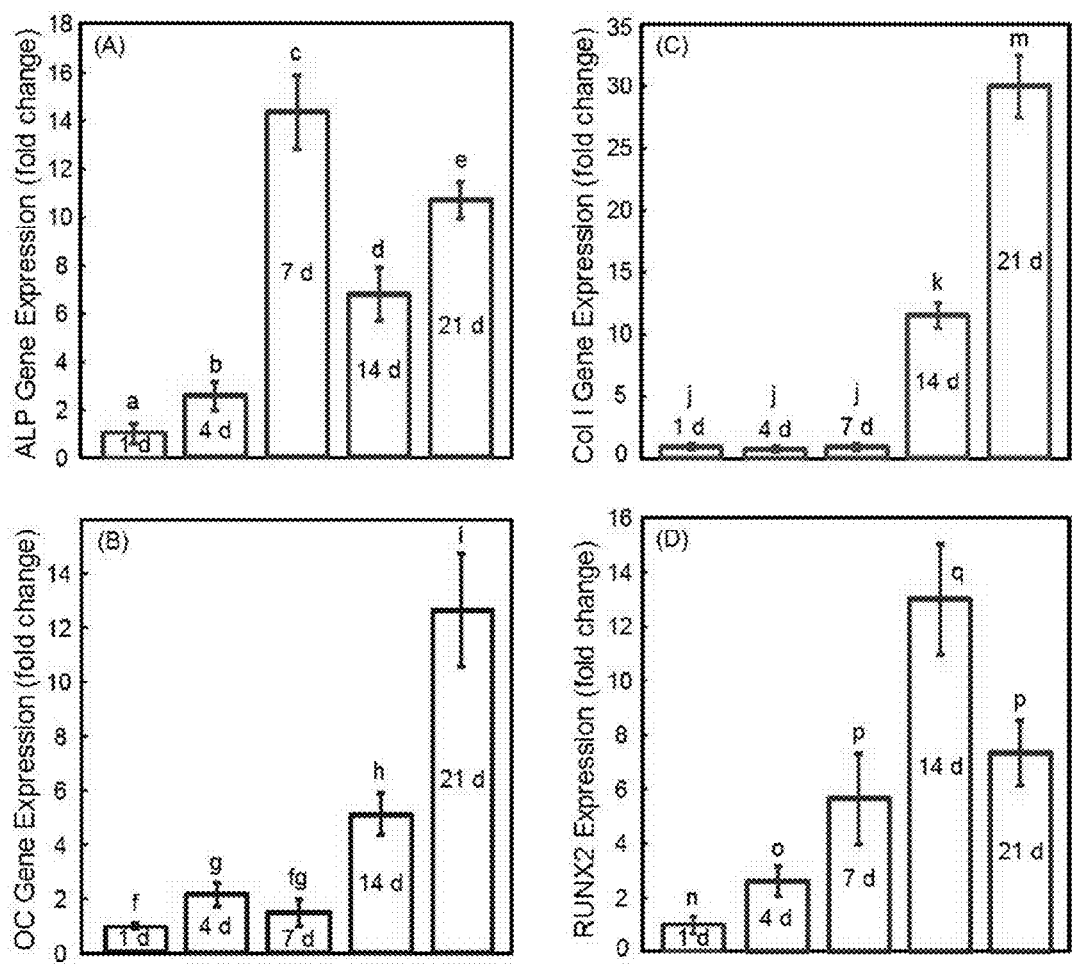

FIG. 10 shows osteogenic differentiation of hUCMSC-encapsulating microbeads in CPC-grafted-RGD surface. (A) ALP, (B) OC, (C) collagen type I, and (D) Runx2 gene expressions, measured by RT-PCR. All four markers reached much higher levels than 1 d, indicating successful osteogenic differentiation of the hUCMSCs released from the microbeads and attached to the CPC-grafted-RGD scaffold. Each value is mean±sd; n=5.

Figure 11:
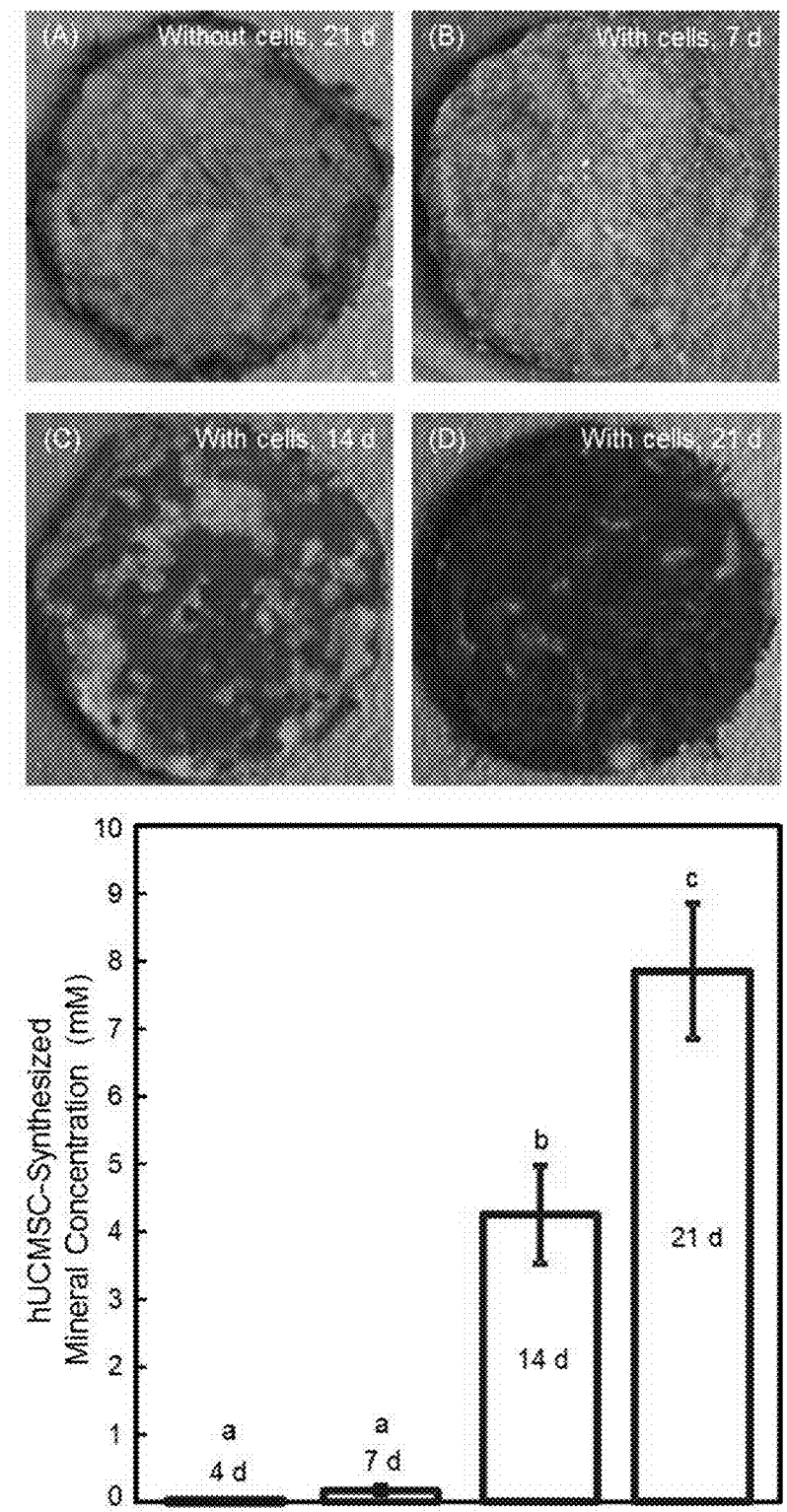

FIG. 11 shows bone mineral synthesis by hUCMSCs released from the microbeads and attached to the CPC-grafted-RGD disks. (A) Disks without cells were immersed as control. (B) Disk with cells at 7 d. (C) Disk with cells at 14 d. (D) Disk with cells at 21 d. The red staining became much thicker and denser over time, and the layer of new mineral matrix synthesized by the cells covered the entire disk at 21 d. (E) Cell-synthesized mineral concentration was measured by the osteogenesis assay. Each value is mean±sd; n=5.

Figure 12:
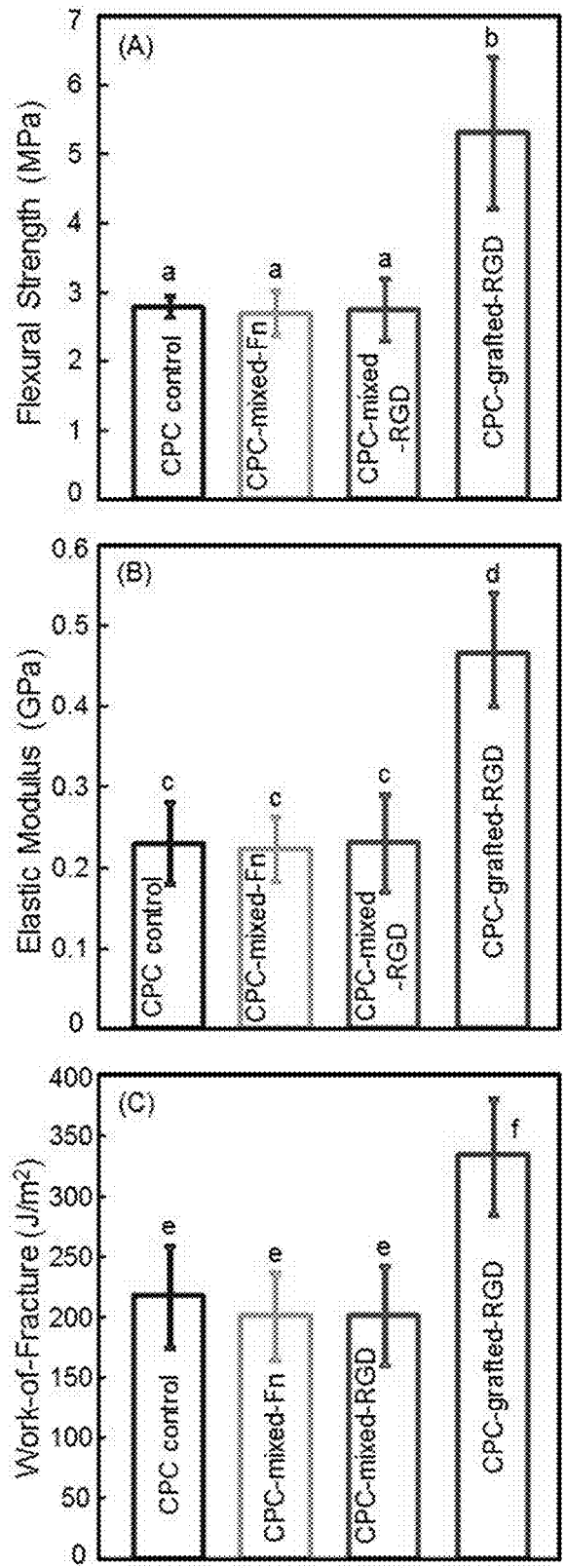

FIG. 12 shows mechanical properties of biofunctionalized CPC containing various biofunctional molecules. (A) Flexural strength, (B) elastic modulus, and (C) work-of-fracture (toughness). Each value is mean±sd; n=5.

DETAILED DESCRIPTION

The need for bone regeneration or remodeling can arise from trauma, disease, congenital deformity, or tumor resection. Stem cell-scaffold approaches hold immense promise for bone tissue engineering. Currently, pre-formed scaffolds for cell delivery have drawbacks, including the difficulty of seeding cells deeply into the scaffold and the inability to inject such scaffolds in repair procedures involving minimally invasive surgeries. Current injectable polymeric carriers and hydrogels are too weak for load-bearing orthopedic application.

Provided herein is an injectable, strong, biofunctional agent-containing bone paste for bone tissue engineering. In the bone pastes described herein, a calcium phosphate cement (CPC) is combined with one or more biofunctional agents. The bone pastes may optionally further comprise cells or cell-encapsulating (e.g., hydrogel) microbeads, where the cells include human umbilical cord mesenchymal stem cells (hUCMSCs) or stem cells from other sources. The CPC may optionally contain chitosan and/or degradable fibers for reinforcement. The CPC may further optionally contain a porogen to increase the porosity of the bone paste. The resulting bone pastes are fully injectable under small injection forces. When cell-encapsulating microbeads are present in the bone paste, the cell viability post-injection matches that in hydrogel without CPC and without injection. Stem cells in the injectable bone pastes maintain their ability to osteodifferentiate, as indicated by expression of osteogenic markers such as alkaline phosphatase and osteocalcin and by accumulation of bone minerals. Mechanical properties of the bone pastes match the reported values of cancellous bone, and are much higher than previous injectable polymeric and hydrogel carriers.

The addition of biofunctional agents such as fibronectin and Arg-Gly-Asp (RGD) peptide improves cell attachment and proliferation [36-45]. Any combination of one or more of the five classes of biofunctional agents may be incorporated into the bone pastes of the present invention. The first class is the RGD-containing peptides, i.e., peptides that contain the sequence RGD, which is a known integrin-recognition site that promotes cell attachment. The second class is fibronectin (Fn), which is a general cell adhesion molecule that anchors cells to collagen and proteoglycan. The third class is fibronectin-like engineered protein polymer (FEPP). The fourth class is extracellular matrix (ECM). The fifth class is platelet concentrate, a fraction of the plasma in which platelets are concentrated.

Bone pastes comprising one of these five classes of biofunctional agents are generally referenced herein as: CPC-RGD, CPC-Fn, CPC-FEPP, CPC-ECM, and CPC-Platelets. Each of these five different types of bone paste substantially enhances stem cell functions, such as those of hUCMSCs. Live cell density and actin stress fibers are greatly increased due to the incorporation of biofunctional agents in CPC. Actin stress fibers anchor to the cell membrane at locations that are frequently connected to the ECM or the scaffold, and these connection sites are called focal adhesions [58]. The mineralization by hUCMSCs is also markedly enhanced by incorporation of biofunctional agents in CPC. Therefore, the biofunctionalized CPCs used in the bone pastes of the present invention should greatly enhance cell function and bone regeneration.

The hUCMSC-microbead-CPC bone pastes described herein are fully injectable; when included, chitosan and fibers increase the mechanical properties, without compromising the injectability, of the pastes. The injection process does not interfere with the osteogenic capacity of the cells contained within the bone pastes, when present. For example, encapsulated hUCMSCs differentiate down the osteogenic lineage, as demonstrated by elevated alkaline phosphatase (ALP) and osteocalcin (OC) gene expression, ALP protein synthesis, and mineralization. Expression of osteogenic markers and mineralization of hUCMSCs in the injectable CPC-based bone pastes matches those in hydrogel without CPC.

Provided below are specific examples of the injectable bone pastes of the present invention. One of ordinary skill in the art will understand that variations of the injectable bone pastes exemplified herein are within the spirit and scope of the invention. For example, as described below, cell types other than hUCMSCs (e.g., but not limited to, stem cells such as hBMSCs and hESCs) can be used in bone pastes comprising cell-encapsulating microbeads. In addition, the size of the microbeads can be varied. For example, the microbeads used in the Examples below have a mean length of approximately 335 µm and a mean width of approximately 232 µm. By varying the air pressure used, the inventors have produced microbeads of mean widths and lengths of from 100 µm to 1500 µm, which are also suitable for injection and creation of macropores in CPC after microbead dissolution. Porogenic factors can be included in the CPC to also control the porosity of the bone pastes. The specific Examples described herein employ alginate-fibrin to fabricate the cell-encapsulating microbeads; however, other hydrogels such as photo-cured hydrogels can be used to make cell-encapsulating microbeads-CPC pastes. While the CPCs described in the Examples use TTCP and DCPA, the cell-encapsulating microbeads can be readily incorporated into other calcium phosphate cements with various chemistry and compositions. The CPCs described in the Examples employ a TTCP:DCPA molar ratio of 1:1 or 1:3. Other TTCP:DCPA ratios (e.g., but not limited to 1:2), and other fiber types, lengths, and volume fractions can be used in the injectable bone pastes for various orthopedic and other bone repair/remodeling applications. Additional examples of variations that can be employed in the bone pastes described herein are set forth below.

Calcium Phosphate Cement Compositions

The CPCs used in the bone pastes of the present invention vary based on the identity and proportions of calcium phosphate components that comprise the CPC. Suitable calcium phosphate components include and are not limited to: tetracalcium phosphate (TTCP) ($Ca_4(PO_4)_2O$), dicalcium phosphate anhydrous (DCPA) ($CaHPO_4$), dicalcium phosphate dihydrate ($CaHPO_4.2H_2O$), tricalcium phosphate ($Ca_3[PO_4]_2$), α-tricalcium phosphate (α-$Ca_3(PO_4)_2$), β-tricalcium phosphate (β-$Ca_3(PO_4)_2$), octacalcium phosphate ($Ca_2H_2(PO_4)_6.5H_2O$), amorphous calcium phosphate ($Ca_3(PO_4)_2$), calcium carbonate ($CaCO_3$), calcium hydroxide ($Ca[OH]_2$), and hydroxyapatite ($Ca_{10}(PO_4)_6(OH)_2$), and mixtures thereof. In one aspect of the invention, the CPC comprises TTCP and DCPA. CPCs comprising TTCP and DCPA can contain various molar ratios of TTCP to DCPA. For example, TTCP:DCPA molar ratios can include ratios from about 1:5 to about 5:1, e.g., about 1:5, about 1:4, about 1:3, about 1:2, about 1:1, about 2:1, about 3:1, about 4:1, about 5:1, about 3:2, about 2:3, about 4:3, about 3:4, about 5:4, about 4:5, and others. An example of an acceptable CPC for use in the bone pastes of the present invention comprises a mixture of TTCP:DCPA in a 1:1 molar ratio or in a 1:3 molar ratio.

The size of the TTCP and DCPA particles used to produce the bone pastes of the present invention may vary depending on the other components of the pastes, and the use to which the paste will be put. However, TTCP and DCPA particles can independently range in size from about 0.1 μm to about 1 mm, from about 0.5 μm to about 500 μm, from about 1 μm to about 100 μm, from about 0.4 μm to about 3 μm, from about 0.5 μm to about 50 μm, from about 5 μm to about 500 μm, or from about 0.5 μm to about 250 μm, for example. TTCP and DCPA particles can also be used that independently have a median size of about 0.05 μm, about 0.1 μm, about 0.5 μm, about 1 μm, about 5 μm, about 10 μm, about 17 μm, about 25 μm, about 50 μm, or about 100 μm, for example.

The liquid portion of the CPC can include, for example, water, chitosan, sodium phosphate, hydroxypropyl methylcellulose, and mixtures thereof.

The CPCs used in the bone pastes of the present invention may also comprise a porogen. The inclusion of a porogen permits the formation of macropores in the CPC. A suitable combination that may serve as a porogen in the CPCs of the present invention is sodium hydrogen carbonate ($NaHCO_3$) and citric acid (e.g., citric acid monohydrate, $C_6H_8O_7.H_2O$). The acid-base reaction of citric acid with $NaHCO_3$ produces $CO_2$ bubbles in CPC, resulting in a macroporous scaffold. $NaHCO_3$ may be added to the CPC powder at a $NaHCO_3$/($NaHCO_3$+CPC powder) mass fractions of from about 0.5% to about 35%, including from about 5% to about 30%, from about 7.5% to about 25%, and from about 10% to about 20%. $NaHCO_3$ may also be added to the CPC powder at a $NaHCO_3$/($NaHCO_3$+CPC powder) mass fraction of about: 5%, 7.5%, 10%, 11%, 12%, 13%, 14%, 15%, 16%, 17%, 18%, 19%, 20%, 22.5%, 25%, 27.5%, and 30%. An amount of citric acid sufficient to maintain a fixed $NaHCO_3$/($NaHCO_3$+$C_6H_8O_7.H_2O$) mass fraction of from about 20% to about 70%, including from about 40% to about 60%, and from about 50% to about 60%. Particular examples include a mass fraction of about: 52.5%, 53%, 53.5%, 54%, 54.5%, 54.52%, 55%, 55.5%, 56%, and 56.5%. Additional porogenic factors that may be used include sugar particles, mannitol particles, salt particles and other agents that can dissolve and degrade to create voids in CPC to increase the porosity.

When forming the bone pastes of the present invention, various ratios of CPC powder to liquid mass can be used, including, but not limited to, 1:5 to about 5:1, e.g., about 1:5, about 1:4, about 1:3, about 1:2, about 1:1, about 2:1, about 3:1, about 4:1, about 5:1, about 3:2, about 2:3, about 4:3, about 3:4, about 5:4, about 4:5, and others.

Biofunctional Agents

In addition to CPC, the bone pastes of the present invention include at least one biofunctional agent selected from the following five classes of biofunctional agents.

The first class is the RGD (Arg-Gly-Asp)-containing peptides. These peptides contain a known integrin-recognition site (RGD) to promote cell attachment [36,36]. RGD is the principle integrin-binding domain present in ECM proteins and it is able to bind multiple integrin species. In addition to RGD peptide itself, RGD-containing peptides include, but are not limited to, the oligopeptides having the following sequences: (Glycine)4-Arginine-Glycine-Aspartic Acid-Serine-Proline (G4RGDSP), Arg-Gly-Asp-Ser (RGDS), Gly-Arg-Gly-Asp (GRGD), Gly-Arg-Gly-Asp-Gly-Tyr (GRGDGY), Arg-Gly-Asp-Ser-Gly-Gly-Cys (RGDSGGC),and Gly-Arg-Gly-Asp-Ser (GRGDS).

The second class is fibronectin (Fn), which is a general cell adhesion molecule that anchors cells to collagen and proteoglycan [40,41]. Fn is also an important ECM protein. It regulates many cellular functions and directs cell adhesion, proliferation, and differentiation via direct interactions with cell surface integrin receptors [40,41]. Fn is synthesized by adherent cells which assemble into a fibrillar network through integrin-dependent and fibronectin-integrin interactions [42].

The third class is fibronectin-like engineered protein polymer (FEPP), which has also been shown to enhance cell adhesion [45-47]. FEPP is genetically-engineered to include 13 copies of the cell attachment epitope of human fibronectin between repeated structural peptide units. It has a stable three-dimensional conformation resistant to thermal and chemical denaturation.

The fourth class is extracellular matrix (ECM). Extracellular matrices (ECMs) can enhance embryonic stem cell culture [48-51]. 3D basement membrane ECMs, such as GELTREX™ (Invitrogen), contain a number of bioactive molecules that enhance cell functions [51]. GELTREX™ is a soluble form of reduced growth factor basement extract, consisting mainly of laminin, collagen IV, entactin, and heparin sulfate proteoglycan, according to the manufacturer. The ECMs that may be used as biofunctional agents also include, but are not limited to, human extracellular matrix (derived from human placenta; BD Biosciences), Matrigel (BD Biosciences), HydroMatrix Peptide Hydrogel (Sigma), and PuraMatrix Peptide Hydrogel (BD Biosciences).

The fifth class is platelet concentrate, which is a fraction of the plasma in which platelets are concentrated [52-54]. It can be obtained by withdrawing blood from the vein of the patient. Platelet concentrate contains a mixture of growth factors which play an important role in wound healing and tissue regeneration [43-45]. Recently, an increasing trend has emerged in the use of autologous platelets to facilitate healing [57]. Platelets have many bioactive proteins responsible for attracting macrophages, MSCs and osteoblasts, which promote removal of necrotic tissue and enhance tissue regeneration and healing. From an initial 30-60 mL of blood withdrawn from a vein, 3-6 mL of platelet-rich plasma can be collected, hence self-production of platelet-rich plasma can be achieved [59,60]. The platelet concentrates that may be used as biofunctional agents include, but are not limited to, autologous platelet concentrate and platelet concentrate from a donor. When the platelet concentrate is from a donor, tissue typing may be performed to ensure compatibility.

The bone pastes of the present invention may include one, two, three, four or all five classes of the biofunctional agents. Thus, bone pastes of the present invention include those having one class of the biofunctional agent, such as CPC-RGD, CPC-Fn, CPC-FEPP, CPC-ECM, and CPC-Platelets; those having two classes of the biofunctional agent, such as CPC-RGD-Fn, CPC-RGD-FEPP, CPC-RGD-ECM, CPC-RGD-Platelets, CPC-Fn-FEPP, CPC-Fn-ECM, CPC-Fn-Platelets, CPC-FEPP-ECM, CPC-FEPP-Platelets, and CPC-ECM-Platelets; those having three classes of the biofunctional agent, such as CPC-RGD-FEPP-Fn, CPC-RGD-ECM-Fn, CPC-RGD- Platelets-Fn, CPC-RGD-ECM-FEPP, CPC-RGD-Platelets-FEPP, CPC-RGD-Platelets-ECM; those having four classes of the biofunctional agent, such as CPC-RGD-Fn-FEPP-ECM, CPC-RGD-FEPP-ECM-Platelets, CPC-RGD-ECM-Platelets-Fn, and CPC-RGD-Platelets-Fn-FEPP; those having all five classes of the biofunctional agent, such as CPC-RGD-Fn-FEPP-ECM-Platelets.

Bone pastes comprising one or more biofunctional agents can be produced by first mixing the agents in the liquid fraction, such as water, and then mixing in CPC powder. Furthermore, RGD peptide can be covalently linked to chitosan, and then dissolved in water, following by mixing in of the CPC powder, when chitosan is included in the bone paste.

The amount of a particular biofunctional agent that is include in a bone paste will vary based on such factors as the identity of the compounds forming the bone paste; the presence or absence of chitosan, fibers, and porogens; the presence or absence of cells or cell-encapsulating microbeads; the identity of the cells; the identity of the microbeads, and the intended use of the bone paste. However, the amount of RGD-containing peptide in the bone paste, when present, will generally be between about 0.0005% and about 5% by mass, or between about 0.001% and about 1% by mass, but is not limited to these ranges. The amount of RGD-containing peptide in the bone paste, when present, can also be considered to be about 0.0005% by mass, about 0.001% by mass, about 0.005% by mass, about 0.01% by mass, about 0.05% by mass, about 0.1% by mass, about 0.5% by mass, or about 1% by mass, but is not limited to these values.

The amount of fibronectin in the bone paste, when present, will generally be between about 0.0005% and about 5% by mass, or between about 0.001% and about 1% by mass, but is not limited to these ranges. The amount of fibronectin in the bone paste, when present, can also be considered to be about 0.0005% by mass, about 0.001% by mass, about 0.005% by mass, about 0.01% by mass, about 0.05% by mass, about 0.1% by mass, about 0.5% by mass, or about 1% by mass, but is not limited to these values.

The amount of FEPP in the bone paste, when present, will generally be between about 0.0005% and about 5% by mass, or between about 0.001% and about 1% by mass, but is not limited to these ranges. The amount of FEPP in the bone paste, when present, can also be considered to be about 0.0005% by mass, about 0.001% by mass, about 0.005% by mass, about 0.01% by mass, about 0.05% by mass, about 0.1% by mass, about 0.5% by mass, or about 1% by mass, but is not limited to these values.

The amount of ECM in the bone paste, when present, will generally be between about 0.01% and about 10% by mass, or between about 0.05% and about 5% by mass, but is not limited to these ranges. The amount of ECM in the bone paste, when present, can also be considered to be about 0.01% by mass, about 0.05% by mass, about 0.1% by mass, about 0.5% by mass, about 1% by mass, about 2% by mass, about 3% by mass, about 4% by mass, or about 5% by mass, but is not limited to these values.

The amount of platelet concentrate in the bone paste, when present, will generally be between about 0.01% and about 10% by mass, or between about 0.05% and about 5% by mass, but is not limited to these ranges. The amount of platelet concentrate in the bone paste, when present, can also be considered to be about 0.01% by mass, about 0.05% by mass, about 0.1% by mass, about 0.5% by mass, about 1% by mass, about 2% by mass, about 3% by mass, about 4% by mass, or about 5% by mass, but is not limited to these values.

When forming the bone pastes of the present invention, the biofunctional agent(s) is mixed with the liquid fraction first, which may include chitosan and/or fibers and/or porogens, and then the CPC powder is mixed in.

Chitosan

The CPCs of the present invention may also contain chitosan. Chitosan content can vary from about 0% to about 50% by mass, for example (but not limited to), 0% to about 5%; about 5 to about 10%; about 10% to about 15%; about 15 to about 20%; about 20 to about 25%; about 25 to about 30%; about 30 to about 35%; about 35 to about 40%; about 40 to about 45%; about 45 to about 50%, by mass, e.g., 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%. Suitable chitosan includes chitosan lactate (Vanson, Redmond, Wash.). One means for producing the bone pastes of the present invention is to dissolve chitosan, such as chitosan lactate, in water to form "chitosan liquid." For example, chitosan lactate can be dissolved in water at a chitosan/(chitosan+water) mass fraction of about 15%. Into the chitosan liquid can then be mixed the fibers and porogens, when present, and the biofunctional agents, followed by CPC powder.

When RGD-containing peptides are included as a biofunctional agent in the bone pastes of the present invention, they may be simply mixed into the chitosan liquid as described above. Alternatively, the RGD-containing peptides may be covalently conjugated to chitosan (RGD grafting), and then dissolved in water to obtain the chitosan liquid. EDC (1-ethyl-3-(3-dimethylaminopropyl) carbodiimide) in combination with sulfo-NHS (N-hydroxysuccinimide) may be used as carboxyl activating agents for the coupling of primary amines to yield amide bonds.

Fibers

The CPCs of the present invention may also contain fibers to strengthen and/or reinforce the bone pastes. Fibers that can be used in the bone pastes of the invention include and are not limited to: rods, fibers, ropes, threads, or meshes. The fibers can be, e.g., glass fibers, ceramic fibers, polymer fibers, metal fibers, or mixtures thereof. Examples include and are not limited to: Type I bovine collagen fibers, poly(L-lactide)-based polymer fibers, glycolic acid-based polymers, and poly(D,L-lactic acid) fibers. The fiber diameters can range from about 100 nm to about 1 mm. The length can range from about 0.1 mm to about 10 mm. The fibers can be non-degradable or degradable. The amount of fibers in the CPC may be based on the volume fraction (vol %) of fibers and includes, e.g., about 0.5% to about 50%, e.g., about: 0.5-5, 5-10, 10-15, 15-20, 20-25, 25-30, 30-35, 35-40, 40-45, and 45-50 vol %, and about: 5 vol %, 10 vol %, 12.5 vol %, 15 vol %, 17.5 vol %, 20 vol %, 22.5 vol %, 25 vol %, 27.5 vol %, 30 vol %, 32.5 vol %, 35 vol %, 37.5 vol %, 40 vol %, 42.5 vol %, 45%, 47.5 vol %, and 50 vol %. The amount of fibers in the CPC may also be based on the mass fraction % of fibers and includes, e.g., about 0.5% to about 50%, e.g., about: 0.5-5, 5-10, 10-15, 15-20, 20-25, 25-30, 30-35, 35-40, 40-45, and 45-50%, and about: 5%, 10%, 12.5%, 15%, 17.5%, 20%, 22.5%, 25%, 27.5%, 30%, 32.5%, 35%, 37.5%, 40%, 42.5%, 45%, 47.5%, and 50%. The concentration of fibers can differ based on the diameter of the fibers as large-diameter fibers that are relatively stiff are less injectable, finer fibers are more flexible and may be more injectable. Vol % equals the volume of fibers/the volume of the complete bone paste. An example of a suitable fiber is an absorbable suture fiber, such as Vicryl™, from Ethicon, Somerville, N.J., and Type I bovine collagen fibers.

Bioactive Agents

The CPCs of the present invention may also contain one or more bioactive agents. There is no particular limitation on the identity of agents that may be utilized, but examples include agents that induce migration of cells to the locus of bone paste application, agents that induce maturation and/or differentiation of cells in the locus of bone paste application, and agents that promote the growth, differentiation, attachment and/or proliferation of the cells encapsulated within the bone paste. Suitable agents include, but are not limited to, cytokines, growth factors, bone morphogenic proteins (e.g. BMP-1, BMP-2, BMP-3, BMP-4, BMP-5, BMP-6, BMP-7, and BMP-8a), hormones, steroids, anesthetics, analgesics, opioids, anti-inflammatory agents, including anti-inflammatory steroid or non-steroidal anti-inflammatory agents, enzyme inhibitors, immunosuppressive agents, growth hormone antagonists, radio- and chemo-therapeutic agents, antimicrobial agents, antibiotics, anti-parasite and/or anti-protozoal compounds, muscle relaxants, anti-spasmodics and muscle contractants including channel blockers, miotics and anti-cholinergics, actin inhibitors, remodeling inhibitors, cell growth inhibitors, anti-adhesion molecules, vasodilating agents, anti-pyretics, anti-angiogenic factors, anti-secretory factors, anti-coagulants and/or anti-thrombotic agents, inhibitors of DNA, RNA or protein synthesis, peptides, proteins, enzymes, lubricants, and imaging agents. In a certain embodiments, the bioactive agent is a drug.

Polymers for Cell Encapsulation

The bone pastes of the present invention may optionally contain microbeads that encapsulate cells, such as stem cells. Hydrogels and biocompatible polymers for cell encapsulation include and are not limited to: alginate, partially oxidized alginate, oxidized alginate, alginate-fibrin, partially oxidized alginate-fibrin, oxidized alginate-fibrin, poly(ethylene glycol diacrylate), poly(ethylene glycol)-anhydride dimethacrylate, gelatin, chemically cross-linked polymers, ionically cross-linked polymers, heat-polymerized polymers, and photopolymerized polymers.

In one aspect, oxidized alginate-fibrin microbeads are used, wherein fibrinogen is added to an alginate solution at a fibrinogen mass fraction of from about 0.05% to about 1% to render microbeads that have sufficient mechanical integrity and that are readably degradable. The fibrinogen may also be added to the alginate solution at a fibrinogen mass fraction of about: 0.05%, 0.06%, 0.07%, 0.08%, 0.09%, 0.10%, 0.11%, 0.12%, 0.13%, 0.14%, 0.15%, 0.16%, 0.18%, 0.20%, 0.22%, 0.24%, 0.26%, 0.28%, 0.30%, 0.32%, 0.34%, 0.36%, 0.38%, 0.40%, 0.42%, 0.44%, 0.46%, 0.48%, 0.50%, 0.52%, 0.54%, 0.56%, 0.58%, 0.60%, 0.62%, 0.64%, 0.66%, 0.68%, 0.70%, 0.72%, 0.74%, 0.76%, 0.78%, 0.80%, 0.82%, 0.84%, 0.86%, 0.88%, 0.90%, 0.92%, 0.94%, 0.96%, 0.98%, or 1%. Alginate oxidized to about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, or more, or less, may be used.

The alginate-fibrin microbeads may be produced by first preparing an oxidized alginate solution by dissolving sodium alginate in water, and adding sodium periodate to induce an oxidization reaction. Ethanol-precipitated product is dissolved in saline, and fibrinogen is added to the solution to yield a mixed alginate-fibrinogen solution. Cells are then added to the oxidized alginate-fibrinogen solution, such as at a density of $1 \times 10^6$ cells/mL. The alginate-fibrinogen droplets are produced as described in PCT/US11/34457 and sprayed into a solution of a calcium chloride and thrombin, where the calcium chloride induces alginate cross-linking, while a reaction between fibrinogen and thrombin produces fibrin.

Hydrogels and biocompatible polymers for cell encapsulation can be formed into microbeads of various diameters for use in the bone pastes described herein. For example, average microbead diameters including but not limited to about 50 μm to about 1500 μm can be used, e.g., about: 50 μm, 75 μm, 100 μm, 200 μm, 300 μm, 400 μm, 500 μmm, 600 μm, 700 μm, 800 μm, 900 μm, 1000 μm, 1100 μm, 1200 μm, 1300 μm, 1400 μm, 1500 μm, and various ranges and mixtures thereof. Smaller and larger bead sizes may be used, as long as they the beads can be easily injected without compromising cell viability. In general, beads should be less than 2 millimeters, so as to minimize cell damage caused by injection of the bone paste.

Examples of volume fractions (vol %) of microbeads for use in the bone pastes described herein are (and are not limited to): about 10% to about 80%, e.g., about: 40-45%, 45-50%, 50-52%; 50-55%, 55-60%, 40-50%, 50-60%, 55-65%, 60-70%, 65-75%, 70-80%, and about: 40%, 45%, 50%, 55%, 60%, 65%, 70%, 75%, 80%, and the like. Vol % equals the volume of microbeads/the volume of the complete bone paste.

The length of time required for microbead degradation and release of the encapsulated cells can be varied depending on the material used to prepare the beads. In some applications, maintaining the cells within the microbeads for a longer period, such as multiple days, weeks, or even months, can be desirable, while in other applications quick release (within hours or a small number of days) can be preferable. When short-term release of cells is required, alginate-fibrin microbeads may be used. Alginate microbeads comprising a small amount of added fibrin have dramatically increased degradation and decreased the release-of-cell times in culture and inside the bone paste. Further, when the cells were released from the degraded microbeads and attached to CPC, they showed a healthy spreading and spindle morphology, consistent with previous studies on cell attachment on CPC surfaces [33].

Cells

Cells that can be encapsulated in the bone pastes and microbeads of the invention include and are not limited to: bone-growing cells, blood vessel-growing cells, and cartilage-growing cells, such as mesenchymal stem cells, embryonic stem cells, umbilical cord stem cells, bone marrow stem cells, lymphoid stem cells, myeloid stem cells, stromal cells, osteogenic cells, osteoblast cells, chondrogenic cells, angiogenic cells, endothelial cells, and mixtures thereof. The noted stem cells include totipotent stem cells, pluripotent stem cells, induced pluripotent stem cells, multipotent stem cells, oligopotent stem cells, unipotent cells, progenitor cells, and osteoblasts. Cells can be human or from any other suitable animal. Breast milk can be used as a source of the stem cells.

Various cell densities can be used in the bone pastes and in the construction of the microbeads encapsulating the cells, e.g. but not limited to, about $10^4$ cells/ml of polymer solution to about $5\times10^6$ cells/ml of polymer solution, e.g., about: $10^4$, $10^5$, $5\times10^5$, $10^6$, $2.5\times10^6$, $5\times10^6$, etc. E.g., one useful range of cell densities is about $5\times10^5$ to about $2\times10^6$, e.g., about $10^6$. After injection of a bone paste containing the cells, cell viability is preferably at least about 50%, e.g, at least about: 50%, 55%, 60%, 65%, 70%, 75%, 80%, 85%, and the like, compared to cell viability before injection.

Bone Paste Kits

The bone pastes of the present invention may be used in a variety of applications and settings. It is clear that one setting is a physician's office or an operating room where the paste is applied to a site of bone injury. The bone pastes may be provided in kits for use in such circumstances where components of the bone pastes are included in the kit and combined on site. The components of such kits may include:

1) A powder and a liquid, which include CPC, one or more biofunctional agents, and optionally, one or more of chitosan, fibers and a porogen 2) Cell-encapsulating microbeads (either from a frozen stock, or freshly encapsulated)

3) Mixing pad, spatula, and an injection syringe system

It will be clear that kits comprising variations on the listed components are encompassed within the scope of the invention and that such variations will be readily apparent to the skilled artisan.

Specific embodiments of the present invention are more particularly described in the following Examples, which are intended as illustrative only, since numerous modifications and variations thereof will be appreciated by those of ordinary skill in the art.

EXAMPLES

Example 1

1A. Materials and Methods 1.1 Fabrication of Biofunctionalized CPC

Tetracalcium phosphate [TTCP: $Ca_4(PO_4)_2O$] was synthesized using equimolar amounts of dicalcium phosphate anhydrous (DCPA: $CaHPO_4$) and calcium carbonate (J. T. Baker, Philipsburg, N.J.). TTCP was ground to obtain particles of 1 to 80 μm, with a median of 17 μm. DCPA was ground to obtain a median particle size of 1 μm. TTCP and DCPA powders were mixed at 1:1 molar ratio to form the CPC powder. Chitosan lactate (Vanson, Redmond, Wash.) was mixed with water at a chitosan/(chitosan+water) mass fraction of 15% to form the liquid, which could cause fast-setting to the CPC paste [55]. For mechanical reinforcement, a resorbable suture fiber (Vicryl, polyglactin 910, Ethicon, N.J.) was cut to filaments of a length of 3 mm and mixed with CPC paste at a fiber volume fraction 20%, following a previous study [55]. The CPC powder to liquid mass ratio of 2:1 was used to form a flowable paste. This CPC is referred to as "CPC control".

Five biofunctionalized CPCs were made by incorporating the following biofunctional agents: RGD, Fn, FEPP, GELTREX™, and platelet concentrate. Each biofunctional agent was mixed with the chitosan liquid, which was then mixed with the CPC powder. The concentration of RGD (Sigma, St. Louis, Mo.) was 50 μg RGD per 1 g of CPC paste (0.005% by mass), following a previous study [38]. For Fn (human plasma Fn, Invitrogen, Carlsbad, Calif.) and FEPP (Sigma), the same 0.005% concentration was used in CPC. GELTREX™ (Invitrogen) was added to CPC at 100 μL GELTREX™ per 1 g of CPC paste (0.1% by mass). This concentration was chosen because preliminary study showed that it did not adversely affect CPC setting time and mechanical property, while greatly improving cell function. Similarly, human platelet concentrate ($1.2\times10^6$ platelets per μL, Biological Specialty Corp., Colmar, Pa.) was added to CPC at 100 μL of platelet concentrate per 1 g of CPC paste (0.1% by mass). CPC containing these agents are referred to as CPC-RGD, CPC-Fn, CPC-FEPP, CPC-GELTREX™, and CPC-Platelets, respectively.

1.2 Setting Time and Mechanical Properties of Biofunctionalized CPC

Setting time of CPC was measured using a method as previously described [56]. Briefly, CPC paste was filled into a mold of 3×4×25 mm and placed in a humidor at 37° C. At one minute intervals, the specimen was scrubbed gently with figures until the powder component did not come off, indicating that the setting reaction had occurred sufficiently to hold the specimen together. The time measured from the powder-liquid mixing to this point was used as the setting time for the specimen [55]. Three specimens were measured for each material (n=3).

To measure mechanical properties, the paste was placed into a mold of 3×4×25 mm. The specimens were incubated at 37° C. for 4 h in a humidor, and then demolded and immersed in water at 37° C. for 20 h. The specimens were then fractured in three-point flexure with a span of 20 mm at a crosshead speed of 1 mm/min on a Universal Testing Machine (5500R, MTS, Cary, N.C.). Flexural strength and elastic modulus were measured (n=6) [35,56].

1.3 hUCMSC Culture hUCMSCs (ScienCell, Carlsbad, Calif.) were derived from the Wharton's Jelly in umbilical cords of healthy babies and harvested as previously described [11,16]. The use of hUCMSCs was approved by the University of Maryland. Cells were cultured in a low-glucose Dulbecco's modified Eagle's medium (DMEM) supplemented with 10% fetal bovine serum (FBS) and 1% penicillin-streptomycin (Invitrogen), which is referred to as the control media. Passage 4 cells were used. The osteogenic media had 100 nM dexamethasone, 10 mM β-glycerophosphate, 0.05 mM ascorbic acid, and 10 nM 1α,25-Dihydroxyvitamin (Sigma) [16,34,35]. A previous study performed immunophenotyping of the hUCMSCs using a flow cytometry method [35]. The hUCMSCs expressed a number of cell surface markers (CD29, CD 44, CD 105, HLA-class I) characteristic of MSCs, and were negative for endothelial marker (CD31) and typical hematopoietic markers (CD34, CD 45). The cells were also negative for HLA Class II [35].

1.4 hUCMSC Adhesion and Proliferation

The materials for the preparation of CPC specimens were sterilized in an ethylene oxide sterilizer (Andersen, Haw River, N.C.) for 12 h and then degassed for 7 d. Each CPC paste was filled into a disk mold with a diameter of 12 mm and a thickness of 1.5 mm. The specimens were incubated at 37° C. for 1 d. Each CPC disk was placed in a well of a 24-well plate, and 50,000 cells in osteogenic medium was added to each well. After 1, 4, and 8 d, the constructs were washed in Tyrode's Hepes buffer, live/dean stained and viewed by epifluorescence microscopy (TE2000S, Nikon, Melville, N.Y.) [35]. Three randomly-chosen fields of view were photographed for each disk. Five disks yielded 15 photos for each material at each time point. $N_{Live}$ is the number of live cells, and $N_{Dead}$ is the number of dead cells.

Live cell density, D, is the number of live cells attached to the specimen divided by the surface area A: $D=N_{Live}/A$ [34,35]. The percentage of live cells is $P=N_{Live}/(N_{Live}+N_{Dead})$.

1.5 Immunofluorescence of Actin Fibers in hUCMSCs on Biofunctionalized CPC

Actin fibers in the cell cytoskeleton were examined to determine if the addition of biofunctional agents in CPC would enhance cell attachment and increase the amount of actin stress fibers. hUCMSC constructs after 1 d culture were washed with PBS, fixed with 4% paraformaldehyde for 20 min, permeabilized with 0.1% Triton X-100 for 5 min, and blocked with 0.1% bovine serum albumin (BSA) for 30 min [35,56]. An actin cytoskeleton and focal adhesion staining kit (Chemicon, Temecula, Calif.) was used, which stained actin fibers into a red color. After incubating the construct with diluted (1:400) TRITC-conjugated phalloidin, cell nuclei were labeled with 4'-6-diamidino-2-phenylindole (DAPI) to reveal the nuclei in blue color. Fluorescence microscopy (Nikon) was used to examine the specimens. The fluorescence of actin fibers in hUCMSCs was measured via a NIS-Elements BR software (Nikon). The actin fluorescence was increased when the actins stress fiber density was increased.

1.6 Osteogenic Differentiation of hUCMSCs on Biofunctionalized CPC

Quantitative real-time reverse transcription polymerase chain reaction measurement (qRT-PCR, 7900HT, Applied Biosystems, Foster City, Calif.) was performed. Cell seeding density of 150,000 cells in osteogenic medium per well was used. Each disk was placed in a well of a 24-well plate. The constructs were cultured in osteogenic media for 1, 4, and 8 d [35]. The total cellular RNA on the scaffolds was extracted with TRIzol reagent (Invitrogen). RNA (50 ng/µl) was reverse-transcribed into cDNA. TaqMan gene expression kits were used to measure the transcript levels of the proposed genes on human alkaline phosphatase (ALP, Hs00758162_m1), osteocalcin (OC, Hs00609452_g1), collagen type I (Coll I, Hs00164004), Runx2 (Hs00231692_m1) and glyceraldehyde 3-phosphate dehydrogenase (GAPDH, Hs99999905). Relative expression for each target gene was evaluated using the $2^{-\Delta\Delta C_t}$ method [57]. The $C_t$ values of target genes were normalized by the $C_t$ of the TaqMan human housekeeping gene GAPDH to obtain the $\Delta C_t$ values. These values were subtracted by the $C_t$ value of the hUCMSCs cultured on tissue culture polystyrene in the control media for 1 d (the calibrator) to obtain the $\Delta\Delta C_t$ values [35].

1.7 hUCMSC Mineralization on Biofunctionalized CPC

Alizarin Red S (ARS) staining was used to visualize bone mineralization by the hUCMSCs [35]. hUCMSCs were seeded on CPC disks and cultured in osteogenic media. After 4 d, 14 d and 21 d, the constructs were stained with ARS. After staining, the cells-scaffold constructs were washed with deionized water for several times with gentle rocking for 5 min for each wash until no dye extraction in the used water was observed. An osteogenesis assay (Millipore, Billerica, Mass.) was used to extract the stained minerals and measure the ARS concentration at $OD_{405}$, following the manufacturer's instructions. ARS standard curve was done with known concentration of the dye. Control scaffolds with the same compositions and treatment, but without hUCMSC seeding, were also measured. The control's ARS concentration was subtracted from the ARS concentration of the scaffold with hUCMSCs, to yield the net mineral concentration synthesized by the cells. The time points of 14 d and 21 d were selected because previous studies found a large increase in calcium content from 12 d to 21 d [58].

One-way and two-way ANOVA were performed to detect significant ($\alpha=0.05$) effects of the variables. Tukey's multiple comparison procedures were used to group and rank the measured values, and Dunn's multiple comparison tests were used on data with non-normal distribution or unequal variance, both at a family confidence coefficient of 0.95.

1B. Results

Figure 1:
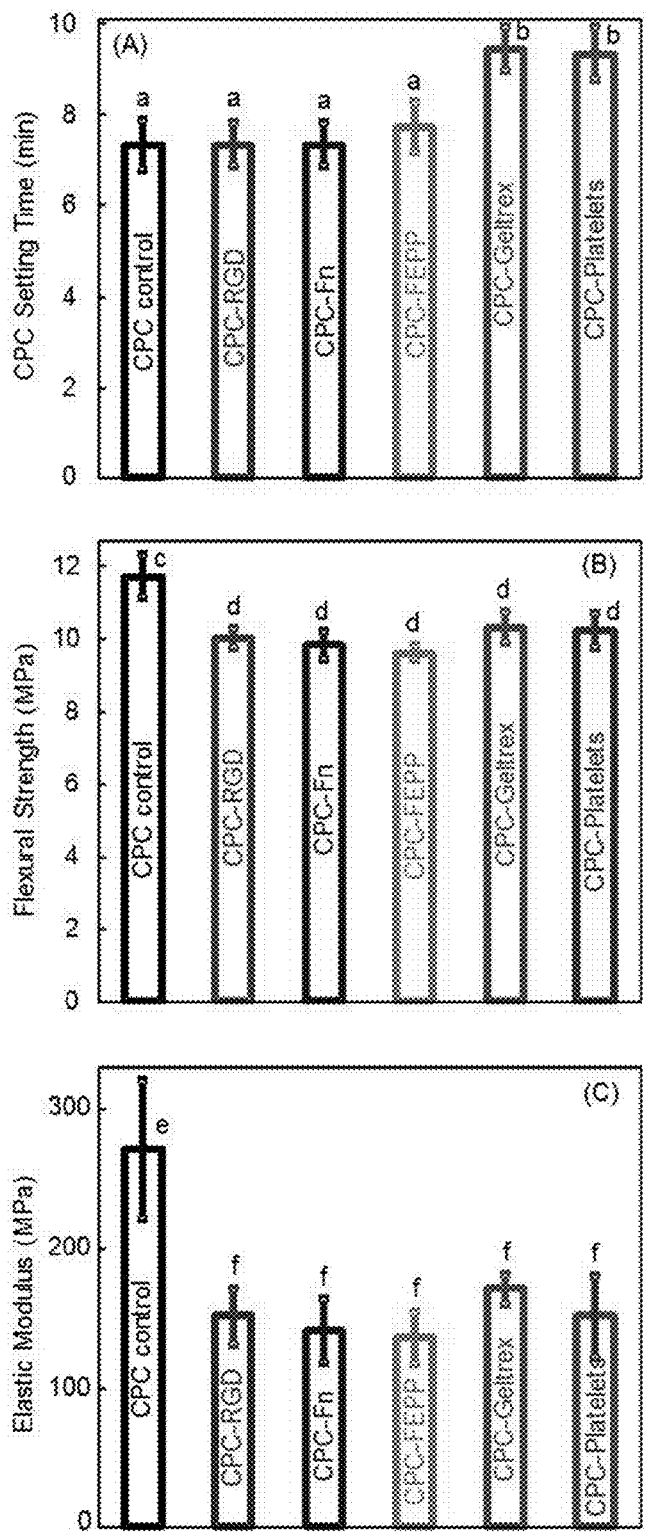
FIG. 1 shows the physical properties of biofunctionalized CPCs. (A) Cement setting time (mean±sd; n=3), (B) flexural strength (mean±sd; n=6), and (C) elastic modulus (mean±sd; n=6). In each plot, bars of values with dissimilar letters are significantly different ($p<0.05$).

FIG. 1 plots the physical properties of biofunctionalized CPC: (A) cement setting time, (B) flexural strength, and (C) elastic modulus (mean±sd; n=6). The setting time was not significantly increased with the addition of RGD, Fn, and FEPP, while that with GELTREX™ and Platelets was slightly increased (p<0.05). The flexural strength was slightly decreased with the addition of biofunctional agents (p<0.05). The elastic moduli of biofunctionalized CPCs were significantly lower than that of CPC control (p<0.05).

Figure 2:
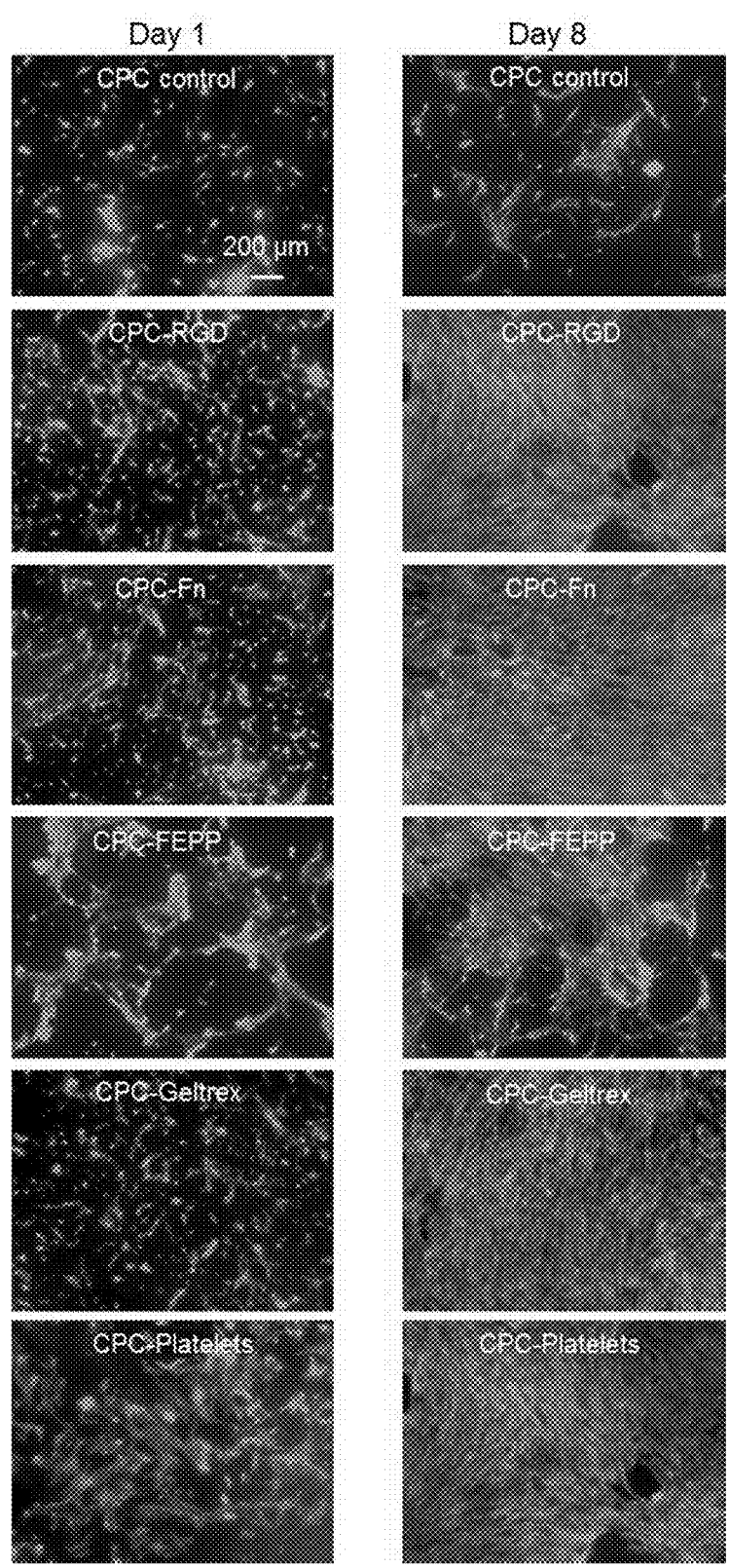
FIG. 2 shows live/dead staining photos of hUCMSCs on biofunctionalized CPC. Live cells showed green fluorescence. Dead cells were stained red. There were numerous live cells and very few dead cells (not shown). At 1 d, there was noticeably more cell attachment to biofunctionalized CPCs than CPC control. Cell density was significantly increased from 1 d to 8 d due to proliferation. There were noticeably more cells on biofunctionalized CPCs than on CPC control.

FIG. 2 shows representative live/dead staining photos. Live cells were stained green and were numerous. Dead cells were stained red and were few (not shown). Adding biofunctional agents into CPC increased the number of live cells attaching to the specimens at 1 d, compared to CPC control. In addition, hUCMSCs on CPC with biofunctional agents had a greater spreading morphology than those on CPC control. Cell proliferation from 1 d to 8 d appeared to be faster on CPC with biofunctional agents than that on CPC control.

Figure 3:
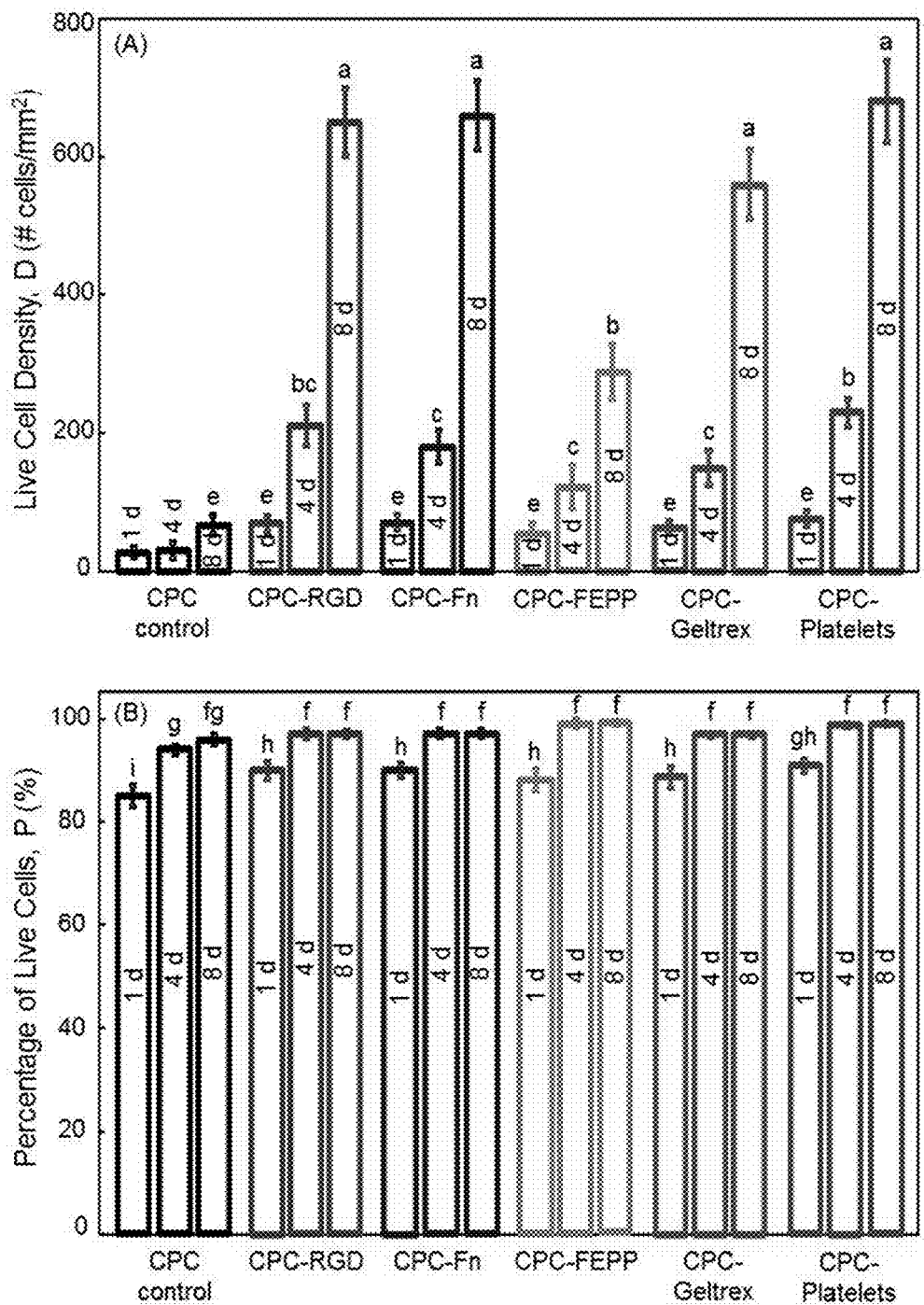
FIG. 3 shows hUCMSC viability on biofunctionalized CPCs: (A) Live cell density, and (B) percentage of live cells. Each value is mean±sd; n=5. In each plot, values with dissimilar letters are significantly different ($p<0.05$).

FIG. 3 plots (A) live cell density, and (B) percentage of live cells. In (A), hUCMSCs proliferated well on all CPC scaffolds, with cell density greatly increasing from 1 d to 8 d. The live cell density was increased by nearly 9-fold from 1 d to 8 d on CPC-RGD, CPC-Fn and CPC-Platelets. At 8 d, live cell density on CPC-RGD, CPC-Fn, CPC-GELTREX™ and CPC-Platelets ranged 600-700 cells/mm$^2$, which was an order of magnitude higher than the 65 cells/mm$^2$ on CPC control. In (B), the percentages of live cells were around 90% at 1 d for all CPCs. There was an increase in the percentage of live cells over time, reaching about 95% at 8 d.

Figure 4:
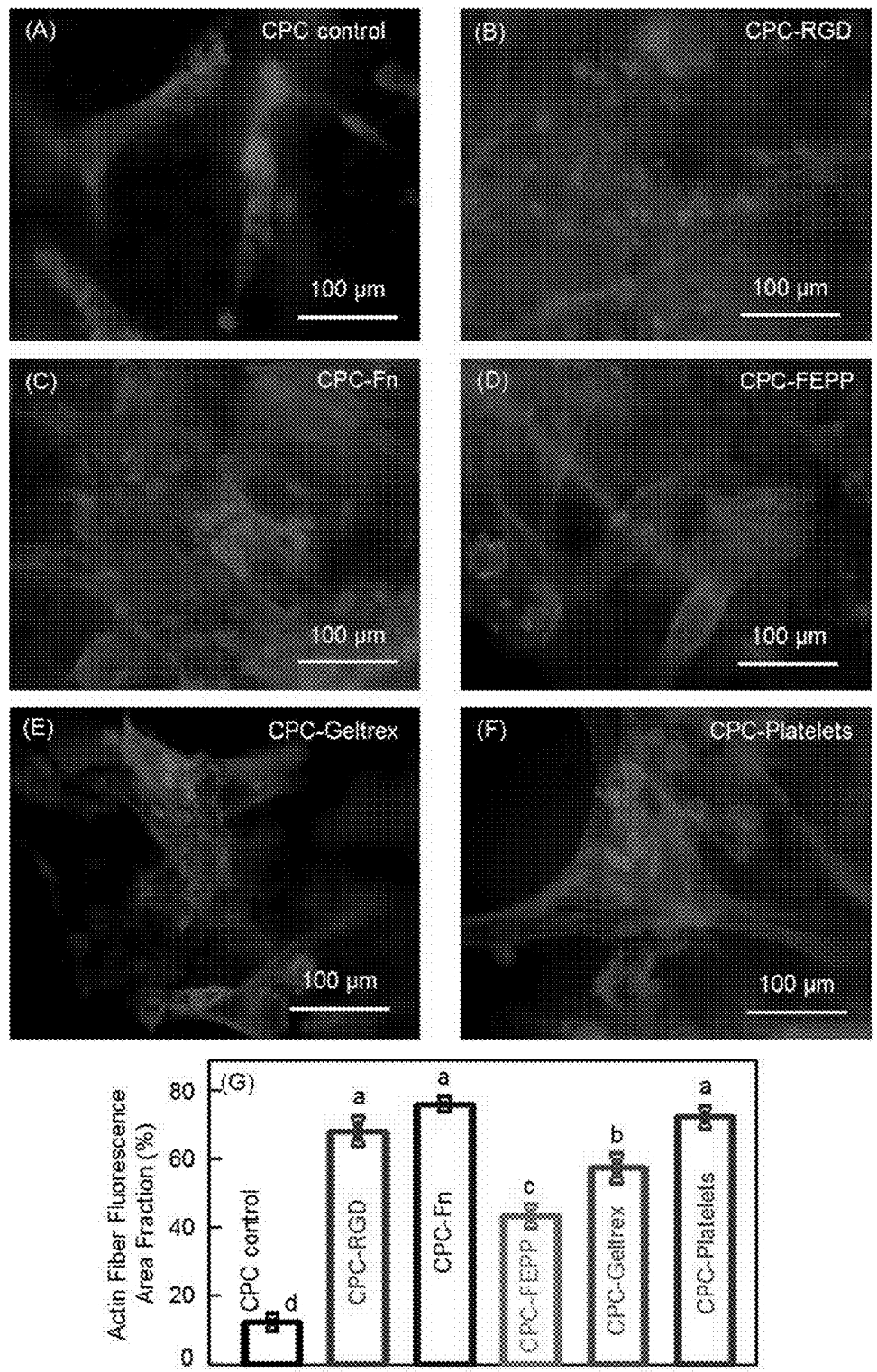
FIG. 4 shows fluorescence of actin fibers in hUCMSCs on biofunctionalized CPCs. (A-F) CPC-RGD, CPC-Fn, CPC-FEPP, CPC-GELTREX™, and CPC-Platelets, respectively. The actin stress fibers in the hUCMSCs were stained red. The cell nuclei (blue fluorescence) indicated the location and distribution of the hUCMSCs on the scaffold. The red color was brighter and denser with the addition of biofunctional agents in CPC. (G) Actin fiber fluorescence area fraction. The area of fluorescence for actin fibers was divided by the total area of the photo. Each value is mean±sd; n=5. Values with dissimilar letters are significantly different ($p<0.05$).

FIG. 4 shows the immunofluorescence of actin fibers. The actin fibers in the cell cytoskeleton were stained a red color. The cell nuclei were fluoresced blue. Compared to CPC control in (A), the red fluorescence was greater in CPC with the five biofunctional agents (B-F), indicating an increased number of actin stress fibers. Extensive networks of actin stress fibers were observed in CPC containing biofunctional agents. In (G), the area of red fluorescence was measured for each image and divided by the image area to yield the area fraction. Compared to CPC control, the actin fiber fluorescence area fraction was increased by 5-7 fold due to the biofunctional agents in CPC.

Figure 5:
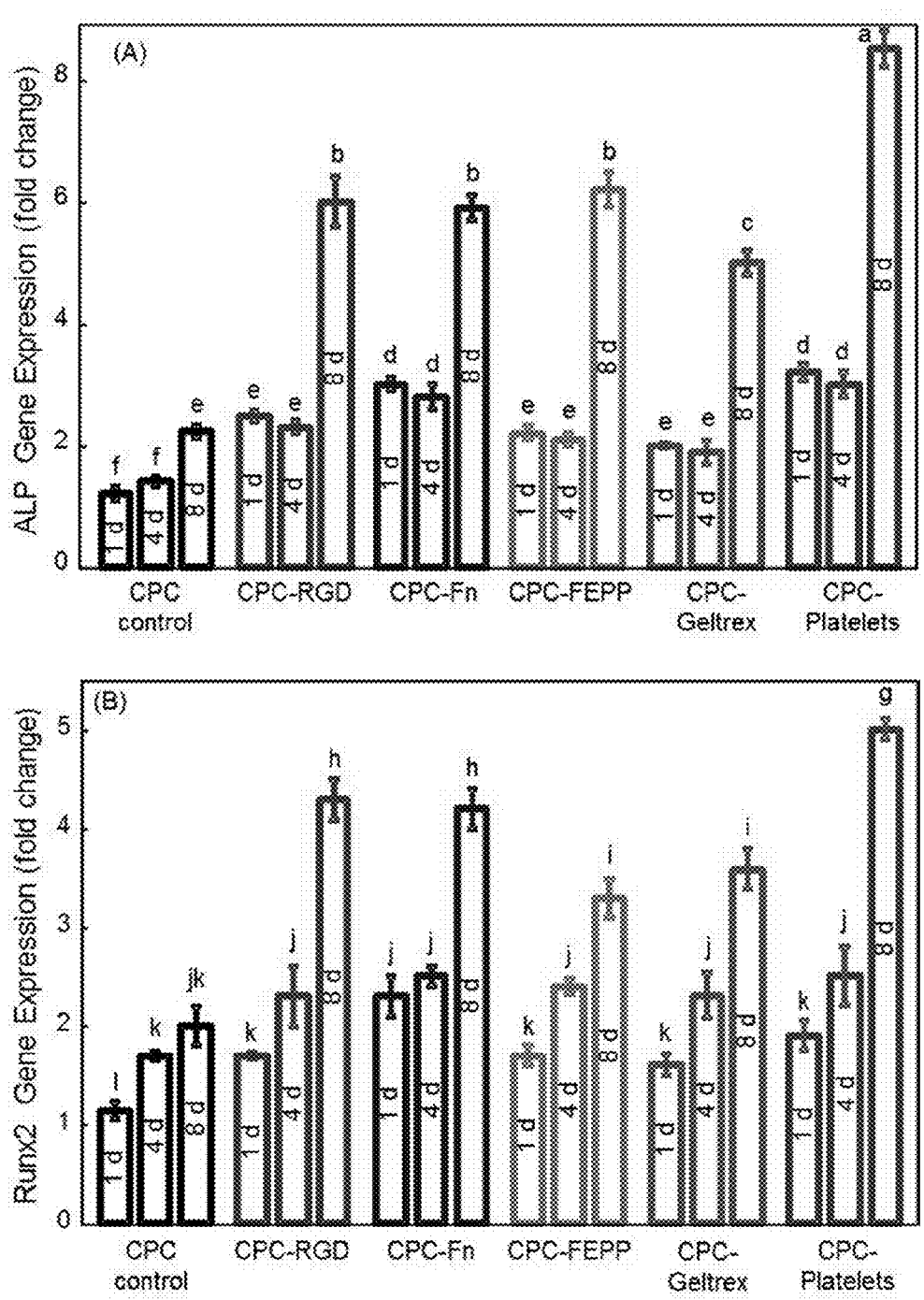
FIG. 5 shows RT-PCR of osteogenic differentiation of hUCMSCs on biofunctionalized CPCs. (A) ALP, (B) Runx2, (C) OC, (D) collagen I gene expressions. Each value is mean±sd; n=5. In each plot, values with dissimilar letters are significantly different ($p<0.05$).
Figure 6:
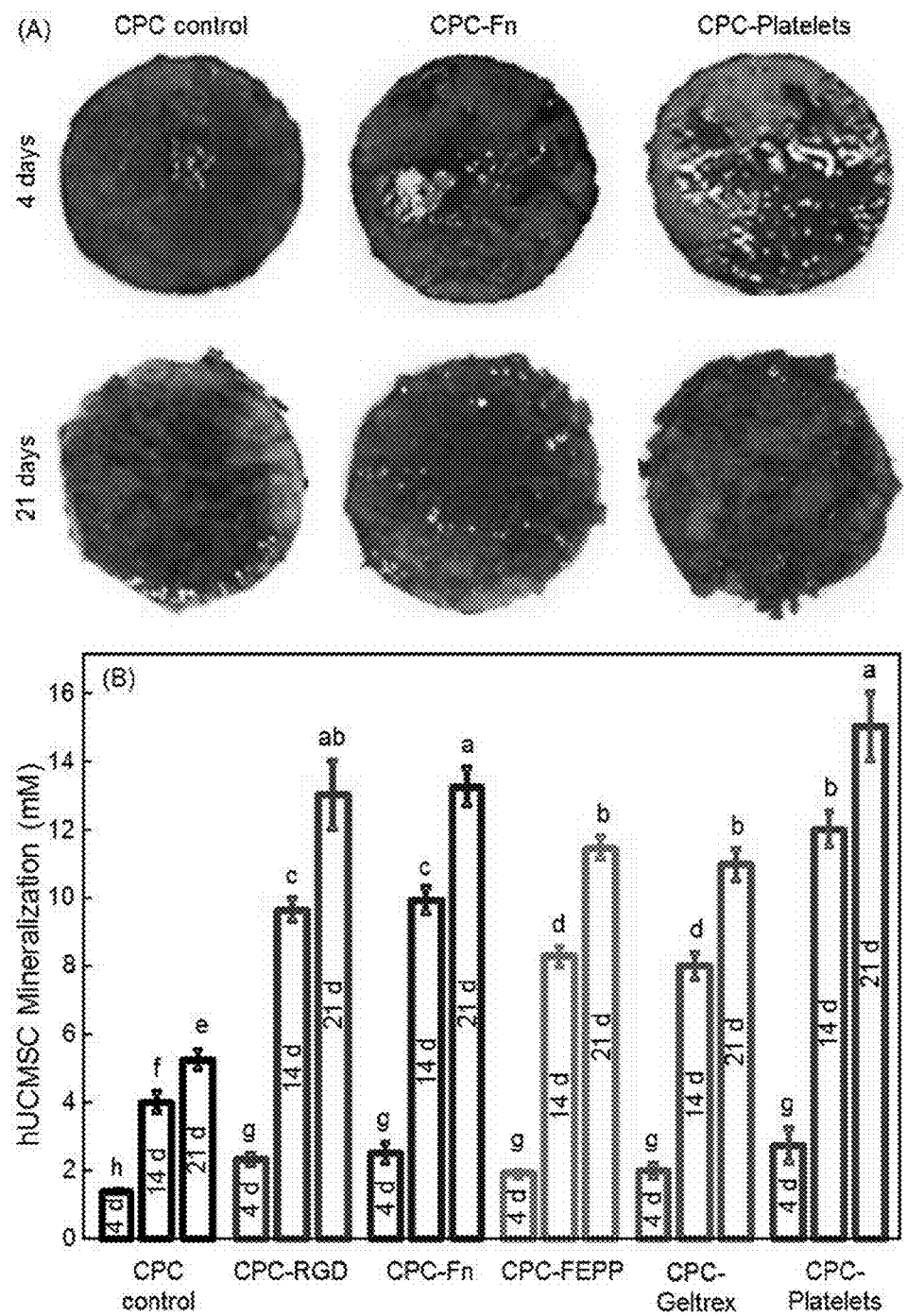
FIG. 6 shows mineral synthesis by hUCMSCs on biofunctionalized CPCs. ARS stained minerals into a red color. (A) ARS staining of hUCMSC-scaffold constructs after 4 d and 21 d, on CPC control, CPC-Fn, and CPC-Platelets, as examples. For all materials, the mineral staining became a thicker and darker red with increasing time from 4 d to 21 d. Between materials, mineralization was thicker and denser on biofunctionalized CPCs than that on CPC control. (B) Mineral concentration synthesized by the hUCMSCs was measured by an osteogenesis assay (mean±sd; n=3). Dissimilar letters at the bars indicate values that are significantly different ($p<0.05$).

Osteogenic gene expressions are plotted in FIG. 5 for: (A) ALP, (B) Runx2, (C) OC, and (D) collagen I. In (A), ALP greatly increased at 8 d. Compared to CPC control, the ALP peak was much higher for all five biofunctionalized CPCs. CPC-Platelets had the highest ALP (p<0.05). In (B), Runx2 had a similar trend as ALP, with all five biofunctionalized CPCs having higher values at 8 d than CPC control. CPC-Platelets had the highest Runx2. In (C) and (D), both OC and collagen I were greatly increased at 8 d. The OC and collagen I peaks were much higher for biofunctionalized CPCs than CPC control (p<0.05).

hUCMSC mineralization is shown in FIG. 6. ARS stained minerals into a red color. In (A), typical staining photos are shown for CPC control, CPC-Fn and CPC-Platelets at 4 d and 21 d, as examples. A thick clump of matrix mineralization synthesized by the cells was observed on at 21 d. ARS staining yielded a red color for CPC without cells, because CPC consisted of hydroxyapatite minerals. However, for CPC with hUCMSCs, the red staining became much thicker and denser over time. There was a layer of new mineral matrix synthesized by the cells that covered the disk, and the mineral staining increased with the addition of biofunctional agents in CPC. In (B), as measured by the osteogenesis assay, the mineral synthesis by the hUCMSCs at 21 d on CPC-Platelets was 3-fold that on CPC control.

The results demonstrate that the novel biofunctionalized CPCs of the present invention greatly improve hUCMSC attachment, proliferation, osteogenic differentiation and mineralization.

Example 2

2A. Materials and Methods 2.1 hUCMSC Culture

Human umbilical cord mesenchymal stem cells (hUCMSCs) were encapsulated in hydrogel microbeads. The cells were obtained from ScienCell (Carlsbad, Calif.), and their use was approved by the University of Maryland. These cells were harvested from the Wharton's Jelly in umbilical cords of healthy babies, using a procedure described previously [63]. The cells were cultured in a low-glucose Dulbecco's modified Eagle's medium (DMEM) with 10% fetal bovine serum (FBS) and 1% penicillin-streptomycin (Invitrogen, Carlsbad, Calif.), which is referred to as the control media. hUCMSCs at 80-90% confluence were detached and passaged. Passage 4 cells were used in this study. The osteogenic media consisted of the control media plus 100 nM dexamethasone, 10 mM β-glycerophosphate, 0.05 mM ascorbic acid, and 10 nM 1α,25-Dihydroxyvitamin (Sigma, St. Louis, Mo.) [64,65].

2.2 Synthesis of Hydrogel Microbeads with hUCMSC Encapsulation

Alginate is non-cytotoxic and can form an ionically-crosslinked network under mild conditions without damaging the encapsulated cells [65-67]. Alginate was oxidized to increase its degradability. Oxidation was done using sodium periodate at the correct stoichiometric ratio of sodium periodate/alginate to have certain percentages of alginate oxidation [61]. The percentage of oxidation (%) was the number of oxidized uronate residues per 100 uronate units in the alginate chain. In a previous study, alginate of up to 5% oxidation was synthesized [61]. In our preliminary studies, the microbeads using 5% oxidized alginate failed to degrade after 21 d in the culture media. This slow degradation may be desirable for other applications, but is too slow for releasing cells in a CPC scaffold. The microbeads using 10% oxidized alginate were too weak to be handled. Hence, in the present study, alginate at 7.5% oxidation was synthesized. The alginate oxidation followed previous procedures [61]. Briefly, 1% by mass of sodium alginate (UP LVG, 64% guluronic acid, MW=75,000-220,000 g/mol, ProNova, Oslo, Norway) was dissolved in distilled water. 1.51 mL of 0.25 mol/L sodium periodate (Sigma) was added to 100 mL of alginate solution, which was stirred to react in the dark at room temperature. At 24 h, the oxidization reaction was stopped by adding 1 g of ethylene glycol and then 2.5 g of sodium chloride. Ethanol of 200 mL was added to precipitate the product, which was then collected by centrifugation. The precipitates were re-dissolved in 100 mL of water and precipitated with 200 mL of ethanol. The second precipitates were collected and dissolved in 30 mL of water. The final product was freeze dried for 24 h, and used to make the microbeads.

The oxidized alginate was dissolved in saline at a concentration of 1.2% [62]. Fibrin was added to the oxidized alginate to obtain oxidized alginate-fibrin microbeads. Fibrinogen from bovine plasma (Sigma) was added at a concentration of 0.1% to the alginate solution and incubated at 37° C. for 2 h to yield a mixed alginate-fibrinogen solution. The fibrinogen concentration of 0.1% was selected because in preliminary studies, fibrinogen>0.1% yielded microbeads that were sticking to each other because fibrin was sticky. Fibrinogen concentration<0.1% resulted in microbeads that were not fast degradable. hUCMSCs were added to the alginate-fibrinogen solution at a density of $1 \times 10^6$ cells/mL. The alginate-cell solution was loaded into a syringe which was connected to a bead-generating device (Var J1, Nisco, Zurich, Switzerland). Nitrogen gas was fed to the gas inlet and a pressure of 8 psi was established to form a coaxial air flow to break up the alginate droplets. To cross-link the microbeads, a solution containing 125 mL of 100 mmol/L calcium chloride plus 125 NIH units of thrombin (Sigma) was prepared. When the alginate-fibrinogen droplets were sprayed into this solution, calcium chloride caused the alginate to crosslink, while the reaction between fibrinogen and thrombin produced fibrin. This yielded hUCMSC-encapsulating, oxidized alginate-fibrin microbeads. A recent study showed that the alginate-fibrin microbeads thus obtained were slightly elongated in shape [62]. The measurement of 100 randomly-selected microbeads showed a length range of 87-580 μm (mean=335 μm), and the width range of 75-345 μm (mean=232 μm) [62]. These oxidized alginate-fibrin microbeads are referred to as "microbeads".

2.3 hUCMSC-encapsulating Microbeads in CPC Surface

The hydrogel microbeads were used to protect the encapsulated cells from the CPC paste mixing forces and the setting reaction. After CPC setting, the purpose was for the microbeads to degrade and release the cells. To examine the effectiveness, the alginate-fibrin microbeads with hUCMSCs encapsulation were seeded into the surface layer of the CPC paste.

The CPC powder consisted of a mixture of tetracalcium phosphate (TTCP), $Ca_4(PO_4)_2O$, and dicalcium phosphate anhydrous (DCPA), $CaHPO_4$. TTCP was synthesized from a reaction between DCPA and $CaCO_3$, and ground to obtain TTCP particles of 1 to 80 μm, with a median of 17 μm. DCPA was ground to obtain particles of 0.4 to 3.0 μm, with a median of 1.0 μm. TTCP and DCPA were mixed at 1:3 molar ratio to form the CPC powder [67]. Type I bovine collagen fiber (Sigma) was added to CPC at a mass fraction of 5.0% collagen/(collagen+CPC) because a previous study showed that collagen in CPC enhanced cell attachment [68]. The CPC liquid consisted of chitosan lactate (Vanson, Redmond, Wash.) dissolved in water at a chitosan/(chitosan+water) mass fraction of 15% [69]. Chitosan and its derivatives are natural biopolymers that are biodegradable and osteoconductive [70], and can impart fast-setting to CPC [55]. A CPC powder to liquid mass ratio of 2:1 to form the CPC paste. The CPC paste was filled into a disk mold of 15 mm diameter and 2 mm height, and the paste surface was flattened with a glass slide. Then, 0.2 mL of hUCMSC-encapsulating microbeads were placed on the CPC paste and gently pressed to be partially embedded into the paste. After incubating for 10 min at 37° C. and 100% humidity, CPC was initially hardened, and the construct was transferred into a 6-well plate. Five mL of osteogenic media was added in each well. After 1 d, CPC was fully set. The microbead-CPC construct is schematically shown in FIG. 7A.

2.4 Development of Novel Biofunctionalized CPC

Preliminary study indicated that after the hUCMSCs were released from the microbeads, the cell attachment on CPC surface was relatively poor and not robust. Therefore, biofunctional molecules were incorporated into CPC to improve cell attachment and function. Four different compositions were tested: CPC control (no addition of biofunctional molecules), CPC mixed with fibronectin, CPC mixed with RGD, and CPC grafted with RGD.

Fibronectin (Fn) from bovine plasma (Sigma) was mixed with the chitosan liquid, which was then mixed with the CPC powder. The reason for using Fn was that Fn was shown to improve cell attachment to scaffolds [71-73]. Based on our preliminary study, 0.25 mg of Fn was mixed in each CPC disk, which was shown to greatly enhance cell function. This biofunctionalized CPC is referred to as "CPC-mixed-Fn".

The tripeptide Arg-Gly-Asp (RGD) is an important functional and cell-binding domain [73-75,80,81]. RGD (Sigma) was mixed with the chitosan liquid, which was then mixed with CPC. As for Fn, 0.25 mg of RGD was mixed into each CPC disk. This biofunctionalized CPC is referred to as "CPC-mixed-RGD".

To further improve cell attachment, instead of simply mixing the RGD into the CPC paste, RGD grafting was performed. Oligopeptides with a sequence of (Glycine)4-Arginine-Glycine-Aspartic Acid-Serine-Proline (abbreviated as G4RGDSP) (Peptides International, Louisville, Ky.) were covalently conjugated to chitosan and then mixed with CPC. EDC (1-ethyl-3-(3-dimethylaminopropyl) carbodiimide) in combination with sulfo-NHS (N-hydroxysuccinimide) were used as carboxyl activating agents for the coupling of primary amines to yield amide bonds. Because EDC is a zero-length crosslinker, polypeptide like G4RGDSP with RGD as the functional sequence is frequently used as cell adhesion peptides for bio-scaffold grafting by carbodiimide chemistry [76,77,80,81]. Briefly, chitosan was dissolved in 0.1 mol/L MES buffer (Sigma) at a mass fraction of 1%. EDC (Sigma), Sulfo-NHS (Sigma), and G4RGDSP peptide were added to the dissolved chitosan at a molar ratio of G4RGDSP/EDC/NHS=1/1.2/0.6, and allowed to react for 24 h. The products were dialyzed against distilled water using a cellulose membrane (MWCO=25 kDa) for 3 d and then freeze dried. This resulted in the RGD-grafted chitosan, which was then dissolved in water at a mass fraction of 15% to obtain the chitosan liquid for mixing with CPC powder. The molecular weight (MW) of G4RGDSP is 759, which is about 2 times the MW (346) of RGD. To use an equivalent amount of the RGD sequence, 0.5 mg of G4RGDSP was immobilized in each CPC disk. This biofunctionalized CPC is referred to as "CPC-grafted-RGD".

Figure 7:
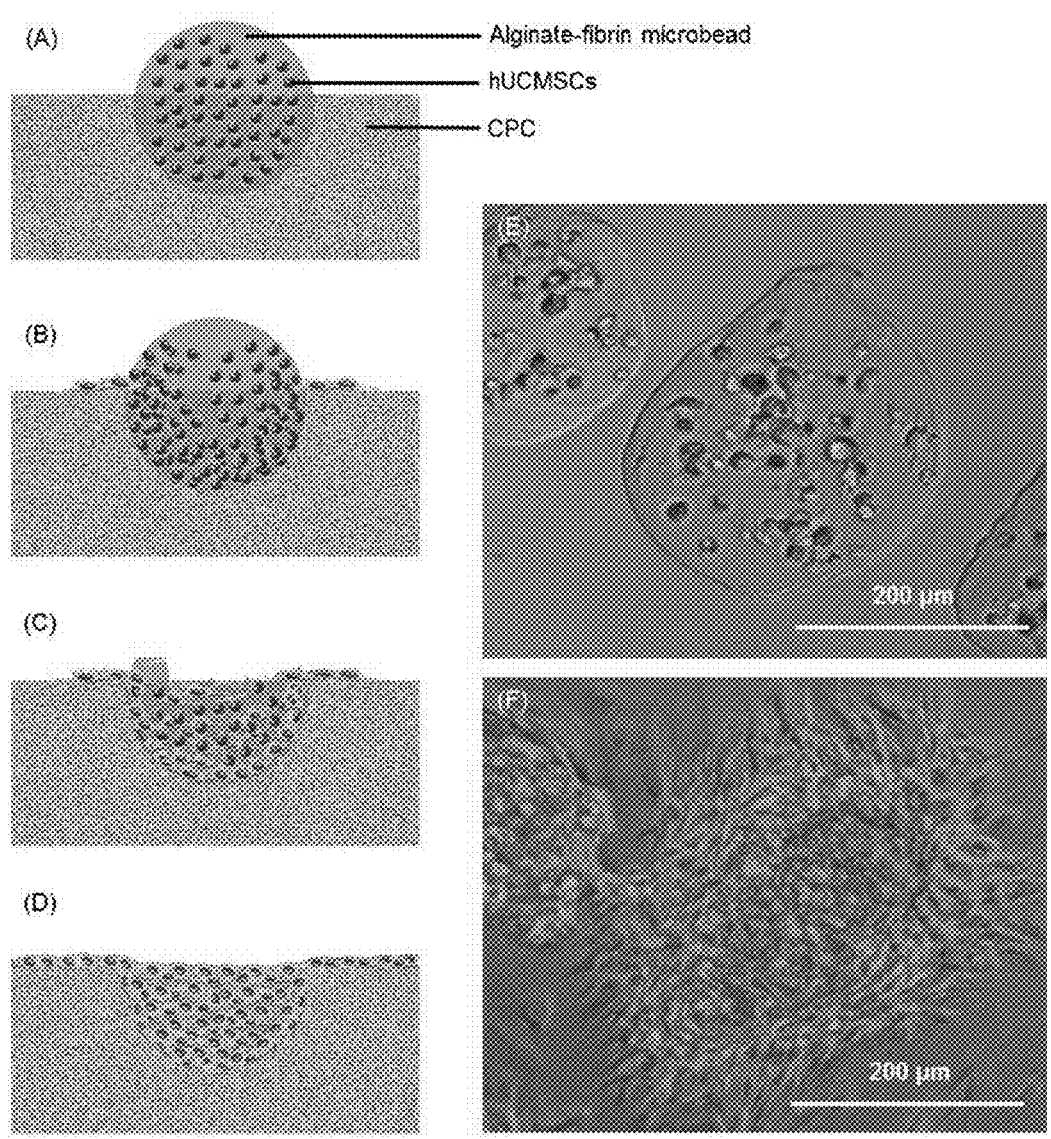
FIG. 7 shows hUCMSC-encapsulating alginate-fibrin microbeads embedded partially into biofunctionalized CPC surface. (A-D) Schematic illustrating microbeads in CPC with cell release at 1 d, 7 d, 14 d and 21 d, respectively. (E, F) Optical photos of microbeads at 1 d and 14 d, respectively. A blue filter was used to enhance the contrast and clarity of microbeads. At 1 d, there was no microbead degradation, and the encapsulated cells appeared as rounded dots. At 14 d, the microbeads degraded and the hUCMSCs were released, showing cell attachment with elongated and spreading morphology.

2.5 Live/Dead Assay of hUCMSCs from Microbeads and Attachment on Biofunctionalized CPC The hUCMSC-encapsulating microbeads were embedded into the surface of the four different types of CPC pastes. The time periods for examination were 1 d, 7 d, 14 d, and 21 d, as schematically shown in FIG. 7 A-D.

For the live/dead staining, each sample was incubated at 37° C. for 10 min with 2 ml Tyrode's Hepes containing 2 µmol/L calcein-AM and 2 µmol/L ethidium homodimer-1 (Molecular Probes, Eugene, Oreg.). This stained live cells into a green color and dead cells into a red color [65]. An epifluorescence microscopy (Eclipse TE2000, Nikon, Melville, N.Y.) was used to examine the samples. Three randomly-chosen fields of view were photographed from each well (six wells yielded 18 photos for each time point). The live and dead cells were counted. The percentage of live cells was: $P_{Live}=N_{Live}/(N_{Live}+N_{Dead})$, where $N_{Live}$=the number of live cells, and $N_{Dead}$=the number of dead cells. The live cell density, $D_{Live}$, was calculated: $D_{Live}=N_{Live}/A$, where A is the area of the view field for $N_{Live}$.

2.6 Osteogenic Differentiation of Released Cells on Biofunctionalized CPC

The above experiments showed that CPC-grafted-RGD had the best cell attachment and proliferation. Hence, CPC-grafted-RGD was selected for osteogenic differentiation experiments. Quantitative real-time reverse transcription polymerase chain reaction (qRT-PCR, 7900HT, Applied Biosystems, Foster City, Calif.) was used. hUCMSC-encapsulating microbeads seeded in the RGD-grafted CPC surface were cultured for 1, 4, 7, 14 and 21 d in osteogenic media. The total cellular RNA of the cells were extracted with TRIzol reagent (Invitrogen) and reverse-transcribed into cDNA using a High-Capacity cDNA Archive kit. TaqMan gene expression assay kits, including two pre-designed specific primers and probes, were used to measure the transcript levels of the proposed genes on human alkaline phosphatase (ALP, Hs00758162_m1), osteocalcin (OC, Hs00609452_g1), collagen type I (Coll I, Hs00164004), runt-related transcription factor 2 (Runx2, Hs00231692_m1), and glyceraldehyde 3-phosphate dehydrogenase (GAPDH, Hs99999905). Relative expression for each gene was evaluated using the 2-$\Delta\Delta C_t$ method [34]. $C_t$ values of target genes were normalized by the $C_t$ of the TaqMan human housekeeping gene GAPDH to obtain the $\Delta C_t$ values. The $C_t$ of hUCMSCs cultured on tissue culture polystyrene in the control media for 1 d served as the calibrator [34,65].

2.7 Mineral Synthesis via hUCMSCs

Mineral synthesis via hUCMSCs released from the microbeads and proliferated on CPC-grafted-RGD was measured. At 4, 7, 14 and 21 d (n=5), Alizarin Red S (ARS) staining was performed to visualize bone mineralization [78]. The CPC-grafted-RGD samples seeded with hUCMSC-microbeads were washed with PBS, fixed with 10% formaldehyde, and stained with ARS (Millipore, Billerica, Mass.) for 5 min, which stained calcium-rich deposits made by the cells into a red color. Controls were incubated in the same manner using CPC-grafted-RGD but without the hUCMSC-encapsulating microbeads. An osteogenesis assay kit (Millipore) was used to extract the stained minerals and measure the Alizarin Red concentration at OD405, following the manufacturer's instructions. The value from the control sample without hUCMSCs was subtracted from the sample seeded with hUCMSCs to obtain the net mineral synthesis by the cells. Time periods of up to 21 d were selected because in previous studies, a great increase in calcium content during in vitro cell cultures was found between 12 d to 21 d [79].

2.8 Mechanical Testing

The purpose of mechanical testing was to investigate the effect of biofunctionalization on CPC mechanical properties. Each CPC composite paste was placed in a rectangular mold of 3×4×25 mm. The specimens were incubated at 37° C. in a humidor for 4 h, and then demolded and immersed in water for 20 h. A three-point flexural test was used to fracture the specimens on a Universal Testing Machine (MTS, Eden Prairie, Minn.) using a span of 20 mm at a crosshead speed of 1 mm/min. Flexural strength, $S=3FL/(2\ bh^2)$, where F is the maximum load on the load-displacement (F-d) curve, L is span, b is specimen width and h is thickness. Elastic modulus $E=(F/d)(L^3/[4\ bh^3])$. Work-of-fracture (toughness) was calculated as the area under the F-d curve divided by the specimen's cross-sectional area [68].

One-way and two-way ANOVA were performed to detect significant ($\alpha=0.05$) effects of the variables. Tukey's multiple comparison tests were used to group and rank the measured values, and Dunn's multiple comparison tests were used on data with non-normal distribution or unequal variance, both at a family confidence coefficient of 0.95.

2B. Results

FIG. 7A-D show the schematic of alginate-fibrin microbead partially embedded in CPC and cultured for 1 d, 7 d, 14 d and 21 d, respectively, illustrating microbead degradation over time, and cell release onto CPC. Optical photos of the microbeads are shown in (E) and (F), at 1 d and 14 d, respectively. Because the microbeads were nearly transparent and difficult to see, a blue filter was used to enhance the contrast and clarity of the microbeads in (E) and (F). These results indicate that the microbeads were degrading over time and the cells were successfully released and migrated out of the macrobeads in (F). Note that the cells encapsulated inside the microbeads appeared as rounded dots in (E), while in (F) the released cells were spreading and elongated in morphology.

Figure 8:
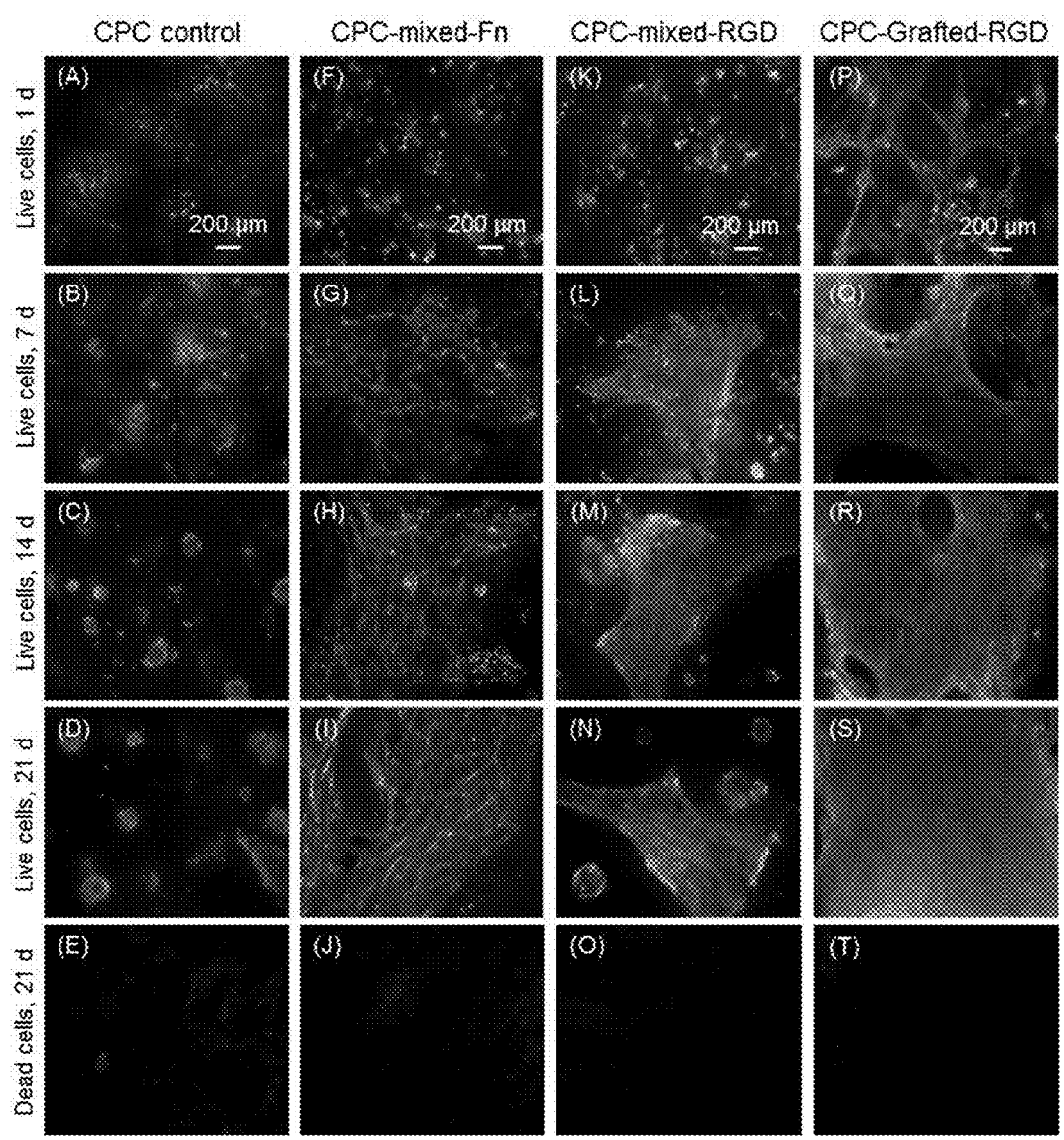
FIG. 8 shows live/dead staining photos of hUCMSC-encapsulating microbeads in the CPC surface. The scaffold type is listed on the top of each column: CPC control, CPC-mixed-Fn, CPC-mixed-RGD, and CPC-grafted-RGD. The culture times are listed on the left side for each row: 1 d, 7 d, 14 d and 21 d. The first four rows show live cells (stained green). The last row shows dead cells (red). There were numerous live cells, and few dead cells. Incorporation of Fn and RGD into CPC increased cell attachment and proliferation. CPC control had the least cells. CPC-grafted-RGD appeared to have the most cells.

The live/dead staining photos are shown in FIG. 8 for hUCMSC-encapsulating microbeads embedded in the surface of CPC control, CPC-mixed-Fn, CPC-mixed-RGD, and CPC-grafted-RGD. At 1 d, 7 d, 14 d and 21 d, the CPC control had limited amount of live cells, consistent with observations in our preliminary study. The released cells did not attach well to CPC, and some cells likely were lost during media change. Noticeable improvements were achieved when Fn or RGD were added to CPC. The cells attached at 7 d and proliferated at 14 d and 21 d. Among the three bioactive agent treatment, CPC-grafted-RGD had the best cell attachment and the fastest cell proliferation. Dead cells (stained red) were shown in FIG. 8 (last row) for 21 d as an example, and there were few dead cells in all cases.

Figure 9:
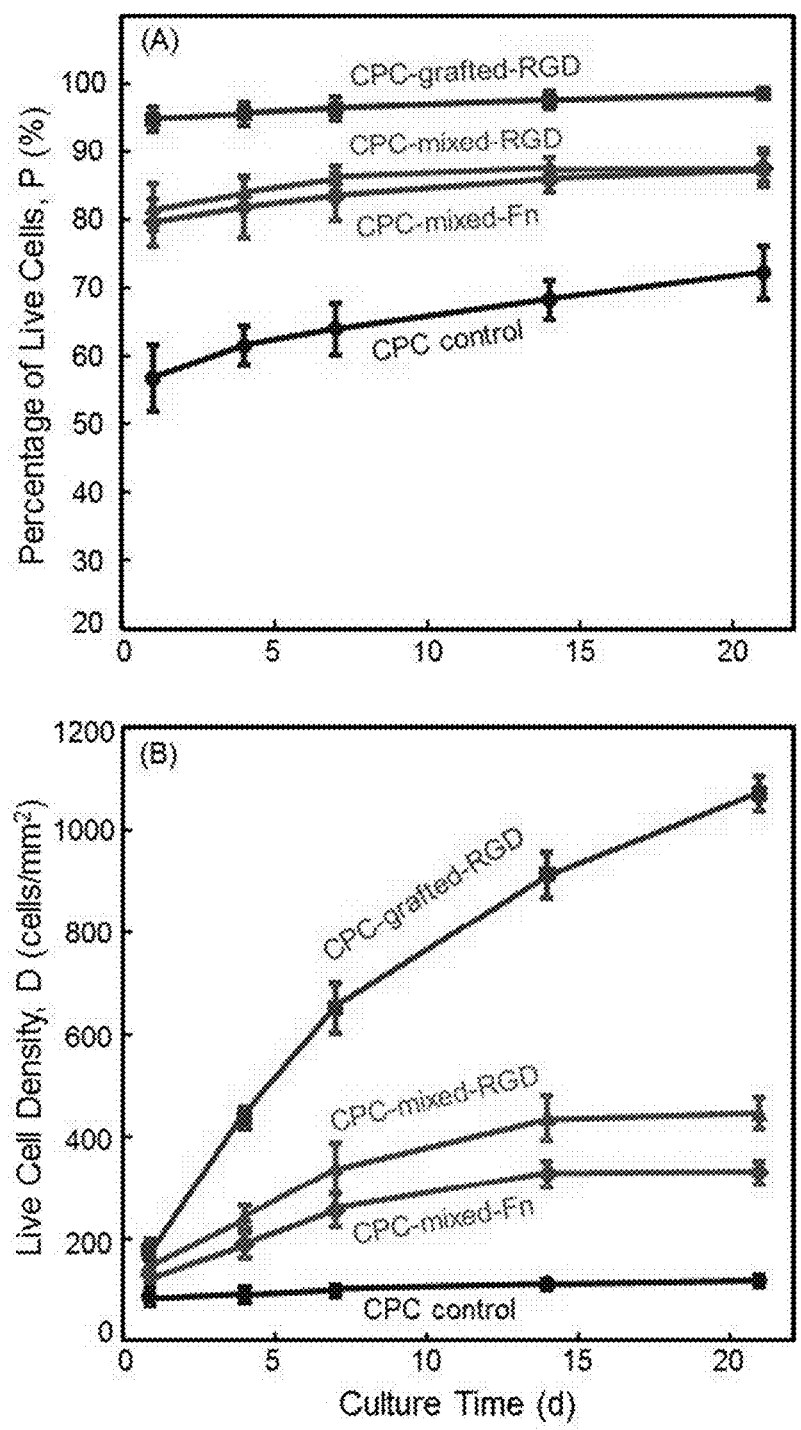
FIG. 9 shows quantitative cell viability of hUCMSCs released from the microbeads and attached to CPC. (A)

FIG. 9 plots (A) the percentage of live cells, and (B) live cell density, for the hUCMSCs released from the microbeads and attached on CPC containing different bioactive agents. In (A), CPC-mixed-Fn and CPC-mixed-RGD had similar percentages of live cells ($p>0.1$), and both were significantly higher than CPC control ($p<0.05$). CPC-grafted-RGD had the highest percentages of live cells among all the groups ($p<0.05$). In (B), the number of live cells per CPC surface area ($mm^2$) increased with increasing culture time due to cell proliferation. Both CPC-mixed-RGD and CPC-mixed-Fn had more live cells than CPC control ($p<0.05$). Among these four groups, CPC-grafted-RGD had dramatically more live cells than the rest. At 21 d, compared to CPC control, the live cell density was increased by 4-fold via mixing the RGD into CPC, and the increase was 9-fold when the RGD was grafted with CPC.

Since CPC-grafted-RGD had the best cell attachment and proliferation, this group was selected for the examination of osteogenic differentiation as a function of culture time. The RT-PCR results are plotted in FIG. 10 for (A) ALP, (B) OC, (C) collagen type I, and (D) Runx2 gene expressions. All four markers reached much higher levels than 1 d, indicating successful osteogenic differentiation of the hUCMSCs released from the microbeads and attached to the CPC-grafted-RGD scaffold.

FIG. 11 shows the mineralization results for hUCMSCs released from the microbeads and attached to the CPC-grafted-RGD disks. Disks without cells were immersed as control for the same time periods, with an example in (A) at 21 d. CPC contained apatite minerals, hence the disks without cells stained a red color. In (B), the disk with cells at 7 d also stained red. However, when the culture time was increased to 14 d and 21 d (C and D, respectively), an additional red substance accumulated on the disks. The red staining became much thicker and denser over time, and the layer of new mineral matrix synthesized by the cells covered the entire disk at 21 d (D). The thick matrix mineralization by the cells covered not only the top surface, but also the peripheral areas at the sides of the scaffold disks at 21 d. The mineral concentration measured by an osteogenesis assay is plotted in (E). The mineral synthesis by the hUCMSCs released from microbeads and attached to CPC-grafted-RGD was minimal at 4 and 7 d, but greatly increased at 14 and 21 d ($p<0.05$).

While adding bioactive agents into CPC improved the function of hUCMSCs, it is important that the CPC mechanical properties are not compromised in order to use the CPC-stem cell construct in load-bearing repairs. FIG. 12 plots the (A) flexural strength, (B) elastic modulus, and (C) work-of-fracture (toughness) of CPC composites. Mixing Fn or RGD into CPC did not decrease the mechanical properties of CPC, compared to that without bioactive agents. CPC grafted with RGD had higher mechanical properties than the other three materials ($p<0.05$).

The results show that (1) hUCMSC-encapsulating alginate-fibrin microbeads in the surface of biofunctionalized CPC released the cells which attached to CPC and differentiated down the osteogenic lineage; and (2) incorporating biofunctional molecules such as RGD and Fn greatly improved the cell function on CPC.

Incorporation by Reference

Throughout this application, various publications, patents, and/or patent applications are referenced in order to more fully describe the state of the art to which this invention pertains. The disclosures of these publications, patents, and/or patent applications are herein incorporated by reference in their entireties to the same extent as if each independent publication, patent, and/or patent application was specifically and individually indicated to be incorporated by reference.

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

[1] Praemer A, Furner S, Rice D P. Musculoskeletal conditions in the United States. Rosemont, Ill.: Amer Acad Orthop Surg; 1999. Chapter 1.

[2] Laurencin C T, Ambrosio A M A, Borden M D, Cooper J A. Tissue engineering: Orthopedic applications. Annual Rev Biomed Eng 1999;1:19-46.

[3] Sikavitsas V I, Bancroft G N, Holtorf H L, Jansen J A, Mikos A G. Mineralized matrix deposition by marrow stromal osteoblasts in 3D perfusion culture increases with increasing fluid shear forces. Proc Natl Acad Sci USA 2003;100:14683-14688.

[4] Mauney J, Volloch V, Kaplan D L. Matrix-mediated retention of osteogenic differentiation potential by human adult bone marrow stromal cells during ex vivo expansion. Biomaterials 2004;25:3233-3243.

[5] Yao J, Radin S, Reilly G, Leboy P S, Ducheyne P. Solution-mediated effect of bioactive glass in poly (lactic-co-glycolic acid)-bioactive glass composites on osteogenesis of marrow stromal cells. J Biomed Mater Res 2005; 75A:794-801.

[6] Mao J J, Giannobile W V, Helms J A, Hollister S J, Krebsbach P H, Longaker M T et al. Craniofacial tissue engineering by stem cells. J Dent Res 2006;85:966-979.

[7] Datta N, Pham Q P, Sharma U, Sikavitsas V I, Jansen J A, Mikos A G. In vitro generated extracellular matrix and fluid shear stress synergistically enhance 3D osteoblastic differentiation. Proceed Natl Acad Sci USA, 2006;103: 2488-2493.

[8] Silva G A, Coutinho O P, Ducheyne P, Reis R L. Materials in particulate form for tissue engineering, Part 2: Applications in bone (review). J Tissue Eng Regen Med 2007;1:97-109.

[9] Mao J J, Vunjak-Novakovic G, Mikos A G, Atala A. Regenerative medicine: Translational approaches and tissue engineering. Artech House, Boston and London, 2007.

[10] Kretlow J D, Young S, Klouda L, Wong M, Mikos A G. Injectable biomaterials for regenerating complex craniofacial tissues. Adv Mater 2009;21:3368-3393.

[11] Wang H S, Hung S C, Peng S T. Mesenchymal stem cells in the Wharton's jelly of the human umbilical cord. Stem Cells 2004;22:1330-1337.

[12] Can A, Karahuseyinoglu S. Concise review: Human umbilical cord stroma with regard to the source of fetus-derived stem cells. Stem Cells 2007;25:2886-2895.

[13] Baksh D, Yao R, Tuan RS. Comparison of proliferative and multilineage differentiation potential of human mesenchymal stem cells derived from umbilical cord and bone marrow. Stem Cells 2007;25:1384-1392.

[14] Bailey M M, Wang L, Bode C J, Mitchell K E, Detamore M S. A comparison of human umbilical cord matrix stem cells and temporomandibular joint condylar chondrocytes for tissue engineering temporomandibular joint condylar cartilage. Tissue Eng 2007;13:2003-2010.

[15] Karahuseyinoglu S, Kocaefe C, Balci D, Erdemli E, Can A. Functional structure of adipocytes differentiated from human umbilical cord stroma-derived stem cells. Stem Cells 2008;26:682-691.

[16] Wang L, Singh M, Bonewald L F, Detamore M S. Signaling strategies for osteogenic differentiation of human umbilical cord mesenchymal stromal cells for 3D bone tissue engineering. J Tissue Eng Regen Med 2009; 3:398-404.

[17] Zhao L, Burguera E F, Xu H H K, Amin N, Ryou H, Arola D D. Fatigue and human umbilical cord stem cell seeding characteristics of calcium phosphate-chitosan-biodegradable fiber scaffolds. Biomaterials 2010;31:840-847.

[18] Jäger M, Degistirici O, Knipper A, Fischer J, Sager M, Krauspe R. Bone healing and migration of cord blood-derived stem cells into a critical size femoral defect after xenotransplantation. J Bone Miner Res 2007;22:1224-1233.

[19] Zhao L, Weir M D, Xu H H K. Human umbilical cord stem cell encapsulation in calcium phosphate scaffolds for bone engineering. Biomaterials 2010;31:3848-3857.

[20] Ducheyne P, Qiu Q. Bioactive ceramics: the effect of surface reactivity on bone formation and bone cell function. Biomaterials 1999;20:2287-2303.

[21] Pilliar R M, Filiaggi M J, Wells J D, Grynpas M D, Kandel R A. Porous calcium polyphosphate scaffolds for bone substitute applications—in vitro characterization. Biomaterials 2001;22:963-972.

[22] Foppiano S, Marshall S J, Marshall G W, Saiz E, Tomsia A P. The influence of novel bioactive glasses on in vitro osteoblast behavior. J Biomed Mater Res A 2004; 71:242-249.

[23] Reilly G C, Radin S, Chen A T, Ducheyne P. Differential alkaline phosphatase responses of rat and human bone marrow derived mesenchymal stem cells to 45S5 bioactive glass. Biomaterials 2007;28:4091-4097.

[24] Deville S, Saiz E, Nalla R K, Tomsia A P. Freezing as a path to build complex composites. Science 2006;311: 515-518.

[25] Drury J L, Mooney D J. Review. Hydrogels for tissue engineering: scaffold design variables and applications. Biomaterials 2003;24:4337-4351.

[26] Brown W E, Chow L C. A new calcium phosphate water setting cement. In: Cements research progress. Brown P W, editor. Westerville, Ohio: Am Ceram Soc. p. 352-379, 1986.

[27] Barralet J E, Gaunt T, Wright A J, Gibson I R, Knowles J C. Effect of porosity reduction by compaction on compressive strength and microstructure of calcium phosphate cement. J Biomed Mater Res B 2002;63:1-9.

[28] Bohner M, Baroud G. Injectability of calcium phosphate pastes. Biomaterials 2005;26:1553-1563.

[29] Link D P, van den Dolder J, van den Beucken J J, Wolke J G, Mikos A G, Jansen J A. Bone response and mechanical strength of rabbit femoral defects filled with injectable CaP cements containing TGF-β1 loaded gelatin microspheres. Biomaterials 2008;29:675-682.

[30] Shindo M L, Costantino P D, Friedman C D, Chow L C. Facial skeletal augmentation using hydroxyapatite cement. Arch Otolaryngol Head Neck Surg 1993;119: 185-190.

[31] Friedman C D, Costantino P D, Takagi S, Chow L C. BoneSource hydroxyapatite cement: a novel biomaterial for craniofacial skeletal tissue engineering and reconstruction. J Biomed Mater Res B 1998;43:428-432.

[32] Xu H H K, Chow L C, Takagi S, Eichmiller F C. Self-hardening calcium phosphate materials with high resistance to fracture, controlled strength histories and tailored macropore formation rates. U.S. Pat. No. 6,955, 716, 2005.

[33] Xu H H K, Zhao L, Detamore M S, Takagi S, Chow L C. 2010, Umbilical cord stem cell seeding on fast-resorbable calcium phosphate bone cement. Tissue Engineering A 16: 2743-2753.

[34] Zhao L, Weir M D, Xu H H K. An injectable calcium phosphate—alginate hydrogel—umbilical cord mesenchymal stem cell paste for bone tissue engineering. Biomaterials 2010;31:6502-6510.

[35] Thein-Han W, Xu H H K. Collagen-calcium phosphate cement scaffolds seeded with umbilical cord stem cells for bone tissue engineering. Tissue Eng 2011 (Epub ahead of print)

[36] Ruoslahti E, Pierschbacher M D. New perspectives in cell adhesion: RGD and integrins. Science 1987:238:491-497.

[37] Bellis S L. Advantages of RGD peptides for directing cell association with biomaterials. Biomaterials 2011;32: 4205-4210.

[38] Schneiders W, Reinstorf A, Pompe W, Grass R, Biewener A, Holch M, Zwipp H, Rammelt S. Effect of modification of hydroxyapatite/collagen composites with sodium citrate, phosphoserine/RGD-peptide and calcium carbonate on bone remodeling. Bone 2007;40:1048-1059.

[39] Sawyer A A, Hennessy K M, Bellis S L. Regulation of mesenchymal stem cell attachment and spreading on hydroxyapatite by RGD peptides and adsorbed serum proteins. Biomaterials 2005;26:1467-1475.

[40] Mosher D F. Fibronectin. Academic Press, INC, 1989.

[41] Hynes R O. Fibronectin. Springer, N.Y., 1990.

[42] Cairns M L, Meenan B J, Burke G A, Boyd B A R. Influence of surface topography on osteoblast response to fibronectin coated calcium phosphate thin films. Colloids Surface B 2010;78:283-290.

[43] Zhang Y, Xiang Q, Dong S, Li C, Zhou Y. Fabrication and characterization of a recombinant fibronectin/cadherin bio-inspired ceramic surface and its influence on adhesion and ossification in vitro. Acta Biomater 2010; 6:776-785.

[44] van den Dolder J, Bancroft G N, Sikavitsas V I, Spauwen P H, Mikos A G, Jansen J A. Effect of fibronectin- and collagen I-coated titanium fiber mesh on proliferation and differentiation of osteogenic cells. Tissue Eng 2003;9:505-515.

[45] Cappello J, Crissman J W. The design and production of bioactive protein polymers for biomedical applications. ACS Polymer Prints 1990;31:193-194.

[46] Esty A. Receptor-specific serum-free cell attachment using a high stable engineered protein polymer. Am Biotechnol Lab 1991;9:44.

[47] Tiwari A, Kidane A, Salacinski H, Punshon G, Hamilton G, Seifalian A M. Improving endothelial cell retention for single stage seeding of prosthetic grafts: use of polymer sequences of arginine-glycine-aspartate. Eur J Vasc Endovasc Surg 2003;25:325-329.

[48] Ilic D. Culture of human embryonic stem cells and the extracellular matrix microenviroment. Regen Med 2006; 1:95-101.

[49] Kim J, Efe J A, Zhu S, Talantova M, Yuan X, Wang S, Lipton S A, Zhang K, Ding S. Direct reprogramming of mouse fibroblasts to neural progenitors. Proc Nat Acad Sci USA 2011;10.1073,1103113108 [Epub ahead of print].

[50] Shaw K R M, Wrobel C N, Brugge J S. Use of three-dimensional basement membrane cultures to model oncogene-induced changes in mammary epithelial morphogenesis. J Mammary Glen Biol Neoplasia 2004;9:293-310.

[51] Eslaminejad M B, Bagheri F, Zomorodian E. Matrigel enhances in vitro bone differentiation of human marrow-derived mesenchymal stem cells. Iranian J Basic Med Sci 2010;13:187-194.

[52] Kasten P, Vogel J, Beyen I, Weiss S, Niemeyer P, Leo A, Lüginbuhl R. Effect of platelet-rich plasma on the in vitro proliferation and osteogenic differentiation of human mesenchymal stem cells on distinct calcium phosphate scaffolds: the specific surface area makes a difference. J Biomater Appl 2008;23:169-188.

[53] Vogel J P, Szalay K, Geiger F, Kramer M, Richter W, Kasten P. Platelet-rich plasma improves expansion of human mesenchymal stem cells and retains differentiation capacity and in vivo bone formation in calcium phosphate ceramics. Platelets 2006;17:462-469.

[54] Kasten P, Vogel J, Luginbühl R, Niemeyer P, Weiss S, Schneider S, Kramer M, Leo A, Richter W. Influence of platelet-rich plasma on osteogenic differentiation of mesenchymal stem cells and ectopic bone formation in calcium phosphate ceramics. Cells Tissues Organs 2006;183: 68-79.

[55] Xu H H K, Takagi S, Quinn J B, Chow L C. Fast-setting calcium phosphate scaffolds with tailored macropore formation rates for bone regeneration. J Biomed Mater Res 2004;68:725-734.

[56] Xu H H K, Simon C G. Self-hardening calcium phosphate composite scaffold for bone tissue engineering. J Orthop Res 2004;22:535-543.

[57] Thein-Han W W, Shah J, Misra R D. Superior in vitro biological response and mechanical properties of an implantable nanostructured biomaterial: Nanohydroxyapatite-silicone rubber composite. Acta Biomater 2009;5: 2668-2679.

[58] Wang Y H, Liu Y, Maye P, Rowe D W. Examination of mineralized nodule formation in living osteoblastic cultures using fluorescent dyes. Biotechnol Prog 2006;22: 1697-1701.

[59] Sampson S, Gerhardt M, Mandelbaum B. Platelet rich plasma injection grafts for musculoskeletal injuries: a review. Curr Rev Musculoskelet Med 2008;1:165-174.

[60] Carlson N E, Roach R B Jr. Platelet-rich plasma: clinical applications in dentistry. J Am Dent Assoc 2002; 133:1383-1386.

[61] Bouhadir, K. H., Lee, K. Y., Alsberg, E., Damm, K. L., Anderson, K. W., and Mooney, D. J. Degradation of partially oxidized alginate and its potential application for tissue engineering. Biotech Progress 17, 945, 2001.

[62] Zhou, H., and Xu, H. H. K. The fast release of stem cells from alginate-fibrin microbeads in injectable scaffolds for bone tissue engineering. Biomaterials 32, 7503, 2011.

[63] Wang, H. S., Hung, S. C., and Peng, S. T. Mesenchymal stem cells in the Wharton's jelly of the human umbilical cord. Stem Cells 22, 1330, 2004.

[64] Baksh, D., Yao, R., and Tuan, R. S. Comparison of proliferative and multilineage differentiation potential of human mesenchymal stem cells derived from umbilical cord and bone marrow. Stem Cells 25, 1384, 2007.

[65] Zhao, L., Weir, M. D., and Xu, H. H. K. Human umbilical cord stem cell encapsulation in calcium phosphate scaffolds for bone engineering. Biomaterials 31, 3848, 2010.

[66] Simon, C. G., Guthrie, W. F., and Wang, F. W. Cell seeding into calcium phosphate cement. J Biomed Mater Res A 68, 628, 2004.

[67] Weir. M, D, Xu, H. H. K., and Simon, C. G., Jr. Strong calcium phosphate cement-chitosan-mesh construct containing cell-encapsulating hydrogel beads for bone tissue engineering. J Biomed Mater Res A 77, 487, 2006.

[68] Moreau, J. L., Weir, M. D., and Xu, H. H. Self-setting collagen-calcium phosphate bone cement: mechanical and cellular properties. J Biomed Mater Res A 91, 605, 2009.

[69] Xu, H. H. K., and Simon, C. G., Jr. Fast setting calcium phosphate-chitosan scaffold: mechanical properties and biocompatibility. Biomaterials 26, 1337, 2005.

[70] Muzzarelli, R. A. A., Biagini, G., Bellardini, M., Simonelli, L., Castaldini, C., and Fraatto, G. Osteoconduction exerted by methylpyrolidinone chitosan in dental surgery. Biomaterials 14, 39, 1993.

[71] Schönmeyr, B. H., Wong, A. K., Li, S., Gewalli, F., Cordiero, P. G., and Mehrara, B. J. Treatment of hydroxyapatite scaffolds with fibronectin and fetal calf serum increases osteoblast adhesion and proliferation in vitro. Plast Reconstr Surg 121, 751, 2008.

[72] Martyn, S. V., Heywood, H. K., Rockett, P., Paine, M. D., Wang, M. J., Dobson, P. J., Sheard, S. J., Lee D, A., and Stark, J. P. Electrospray deposited fibronectin retains the ability to promote cell adhesion. J Biomed Mater Res B 96, 110, 2011.

[73] Place, E. S., Evans, N. D., and Stevens, M. M. Complexity in biomaterials for tissue engineering. Nat Mater 8, 457, 2009.

[74] Barker, T. H. The role of ECM proteins and protein fragments in guiding cell behavior in regenerative medicine. Biomaterials 32, 4211, 2011.

[75] Hsiong, S. X., Boontheekul, T., Huebsch, N., and Mooney, D. J. Cyclic arginine-glycine-aspartate peptides enhance three-dimensional stem cell osteogenic differentiation. Tissue Eng Part A 15, 263, 2009

[76] Grellier, M., Granja, P. L., Fricain, J. C., Bidarra, S. J., Renard, M., Bareille, R., Bourget, C., Amédée, J., and Barbosa, M. A. The effect of the co-immobilization of human osteoprogenitors and endothelial cells within alginate microspheres on mineralization in a bone defect. Biomaterials 30, 3271, 2009.

[77] Ho, M. H., Wang, D. M., Hsieh, H. J., Liu, H. C., Hsien, T. Y., Lai, J. Y., and Hou, L. T. Preparation and characterization of RGD-immobilized chitosan scaffolds. Biomaterials 26, 3197, 2005.

[78] Kim, K., Dean, D., Mikos, A. G., and Fisher, J. P. Effect of initial cell seeding density on early osteogenic signal expression of rat bone marrow stromal cells cultured on cross-linked poly(propylene fumarate) disks. Biomacromolecules 10, 1810, 2009.

[79] Wang, Y. H., Liu, Y., Maye, P., and Rowe, D. W. Examination of mineralized nodule formation in living osteoblastic cultures using fluorescent dyes. Biotechnol 22, 1697, 2006.

[80] Hill, E., Boontheekul, T., and Mooney, D. J. Designing scaffolds to enhance transplanted myoblast survival and migration. Tissue Eng 12, 1295, 2006.

[81] Salinas, C. N., and Anseth, K. S. The influence of the RGD peptide motif and its contextual presentation in PEG gels on human mesenchymal stem cell viability. J Tissue Eng Reg Med 2, 296, 2008.

What is claimed is:

1. A bone paste comprising calcium phosphate cement, one or more biofunctional agents and stem cells, wherein the biofunctional agents are selected from the group consisting of RGD-containing peptides, fibronectin, fibronectin-like engineered polymer protein (FEPP), derived extracellular matrix (dECM), and platelet concentrate, and wherein the stem cells are selected from the group consisting of human umbilical cord mesencchymal stem cells, bone marrow stem cells, embryonic stem cells, pluripotent stem cells, induced pluripotent stem cells, multipotent stem cells, progenitor cells, and osteoblasts.

2. The bone paste of claim 1, wherein the bone paste comprises calcium phosphate cement, an RGD-containing peptide and stem cells, wherein RGD-containing peptide is selected from the group consisting of RGD, G4RGDSP, RGDS, GRGD, GRGDGY, RGDSGGC, and GRGDS, and wherein RGD-containing peptide is present within a range of about 0.0005% to about 5% by mass.

3. The bone paste of claim 1, wherein the bone paste comprises calcium phosphate cement, fibronectin and stem cells, wherein fibronectin is present within a range of about 0.0005% to about 5% by mass.

4. The bone paste of claim 1, wherein the bone paste comprises calcium phosphate cement, FEPP and stem cells, wherein FEPP is present within a range of about 0.0005% to about 5% by mass.

5. The bone paste of claim 1, wherein the bone paste comprises calcium phosphate cement, and stem cells, wherein dECM is present within a range of about 0.001% to about 10% by mass.

6. The bone paste of claim 1, wherein the bone paste comprises calcium phosphate cement, platelet concentrate and stem cells, wherein platelet concentrate is present within a range of about 0.001% to about 10% by mass.

7. The bone paste of claim 1, wherein the bone paste comprises calcium phosphate cement, any two of the biofunctional agents and stem cells.

8. The bone paste of claim 1, wherein the bone paste comprises calcium phosphate cement, any three of the biofunctional agents and stem cells.

9. The bone paste of claim 1, wherein the bone paste comprises calcium phosphate cement, any four of the biofunctional agents and stern cells.

10. The bone paste of claim 1, wherein the bone paste comprises calcium phosphate cement, each of the five biofunctional agents and stem cells.

11. The bone paste of claim 1, wherein the calcium phosphate cement comprises one or more ingredients selected from the group consisting of tetracalcium phosphate (TTCP) ($Ca_4(PO_4)_2O$), dicalcium phosphate anhydrous (DCPA) ($CaHPO_4$), dicalcium phosphate dihydrate ($CaHPO_4 \cdot 2H_2O$), tricalcium phosphate ($Ca_3[PO_4]_2$), α-tricalcium phosphate (α-$Ca_3(PO_4)_2$), β-tricalcium phosphate (β-$Ca_3(PO_4)_2$), octacalcium phosphate ($Ca_8H_2(PO_4)_6 \cdot 5H_2O$), amorphous calcium phosphate ($Ca_3(PO_4)_2$), calcium carbonate ($CaCO_3$), calcium hydroxide ($Ca[OH]_2$), and hydroxyapatite ($Ca_{10}(PO_4)_6(OH)_2$), and mixtures thereof.

12. The bone paste of claim 1, wherein the calcium phosphate cement comprises tetracalcium phosphate and dicalcium phosphate anhydrous.

13. The bone paste of claim 12, wherein the calcium phosphate cement comprises a molar ratio of tetracalcium phosphate to dicalcium phosphate anhydrous of about 1:5 to about 5:1.

14. The bone paste of claim 1, wherein the calcium phosphate cement further comprises chitosan, degradable fibers, or both chitosan and degradable fibers.

15. The bone paste of claim 1, wherein the calcium phosphate cement further comprises a porogen.

16. The bone paste of claim 14, wherein the bone paste comprises calcium phosphate cement, a RGD-containing peptide and stem cells, wherein the RGD-containing peptide is present within a range of about 0.0005% to about 0.05% by mass of the bone paste, and wherein the RGD-containing peptide is covalently linked to said chitosan.

17. The bone paste of claim 1, wherein the cells are attached to a surface of the bone paste, or the cells are interspersed throughout the bone paste, or both.

18. The bone paste of claim 1, wherein the stem cells are encapsulated in microbeads.

19. The bone paste of claim 18, wherein the microbeads are hydrogel microbeads.

20. The bone paste of claim 19, wherein the microbeads are comprised of alginate, partially oxidized alginate, oxidized alginate, alginate-fibrin, partially oxidized alginate-fibrin, oxidized alginate-fibrin, poly(ethylene glycol diacrylate), poly(ethylene glycol)-anhydride dimethacrylate, gelatin, chemically cross-linked polymers, ionically cross-linked polymers, heat-polymerized polymers, or photopolymerized polymers.

21. The bone paste of claim 18, wherein the microbeads are alginate-fibrin microbeads, and wherein the alginate-fibrin microbeads comprise a fibrinogen mass fraction of from about 0.05% to about 1%.

22. The bone paste of claim 21, wherein the alginate is at about 7.5% oxidation.

23. The bone paste of claim 18, wherein the microbeads have an average diameter of less than about 2 millimeters.

\* \* \* \* \*